(12) United States Patent
Fromovich et al.

(10) Patent No.: US 8,197,255 B2
(45) Date of Patent: Jun. 12, 2012

(54) CONDENSING SKELETAL IMPLANT THAT FACILITATE INSERTIONS

(75) Inventors: Ophir Fromovich, Petach Tikva (IL); Yuval Jacoby, Tel Aviv (IL); Nitzan Bichacho, Tel Aviv (IL); Ben-Zion Karmon, Petach Tikva (IL)

(73) Assignee: Nobel Biocare Services AG, Flughafen (CH)

( * ) Notice: Subject to any disclaimer, the term of this patent is extended or adjusted under 35 U.S.C. 154(b) by 0 days.

(21) Appl. No.: 12/552,211

(22) Filed: Sep. 1, 2009

(65) Prior Publication Data

US 2009/0325126 A1 Dec. 31, 2009

Related U.S. Application Data

(63) Continuation of application No. 10/558,260, filed on Dec. 21, 2006, now Pat. No. 7,597,557, which is a continuation of application No. PCT/IL2004/000438, filed on May 23, 2004.

(30) Foreign Application Priority Data

May 21, 2003 (IL) .......................................... 156033

(51) Int. Cl.
*A61C 8/00* (2006.01)
(52) U.S. Cl. ...................................................... 433/174
(58) Field of Classification Search .......... 433/173–175, 433/201.1, 215
See application file for complete search history.

(56) References Cited

U.S. PATENT DOCUMENTS

| | | | |
|---|---|---|---|
| 1,698,951 A | 1/1929 | Holmes | |
| 2,215,770 A | 9/1940 | Sheffield | |
| 3,672,058 A | 6/1972 | Nikoghossian | |
| 3,797,113 A | 3/1974 | Brainin | |
| 3,849,887 A | 11/1974 | Brainin | |

(Continued)

FOREIGN PATENT DOCUMENTS

DE     10231743 A1     2/2004

(Continued)

OTHER PUBLICATIONS

Fernandes, Americo, DMD, "Combining the Single Implant With a CAD/CAM Restoration", Dentistry Today, vol. 20 No. 12, dated Dec. 2001. (Note Figure 9).

(Continued)

*Primary Examiner* — Cris L Rodriguez
*Assistant Examiner* — Hao D Mai
(74) *Attorney, Agent, or Firm* — Knobbe, Martens, Olson & Bear, LLP.

(57) ABSTRACT

A dental implant that facilitates insertion includes a body having a coronal end and an apical end opposite the coronal end. An implant-prosthetic interface region is provided adjacent the coronal end. A tapered region is adjacent the apical end. A variable profile helical thread extends along the tapered region. The thread becomes broader in the apical-coronal direction and higher in the coronal-apical direction. The threads include an apical side, a coronal side and a lateral edge connecting them. The variable profile thread includes an expanding length of the lateral edge while the distance of the lateral edge from the base is reduced in the direction of the coronal end. The implant also has a gradual compressing tapered core, a self drilling apical end with a spiral tap, and a coronal end with and inverse tapering.

17 Claims, 16 Drawing Sheets

U.S. PATENT DOCUMENTS

| | | | |
|---|---|---|---|
| 4,103,422 A | 8/1978 | Weiss et al. | |
| 4,406,623 A | 9/1983 | Grafelmann et al. | |
| 4,431,416 A | 2/1984 | Niznick | |
| 4,468,200 A | 8/1984 | Munch | |
| 4,547,157 A | 10/1985 | Driskell | |
| 4,645,453 A | 2/1987 | Niznick | |
| 4,713,003 A | 12/1987 | Symington et al. | |
| 4,738,623 A | 4/1988 | Driskell | |
| 4,758,161 A | 7/1988 | Niznick | |
| 4,812,120 A * | 3/1989 | Flanagan et al. | 433/173 |
| 4,826,434 A | 5/1989 | Krueger | |
| 4,863,383 A | 9/1989 | Grafelmann | |
| 4,932,868 A | 6/1990 | Linkow et al. | |
| 4,960,381 A | 10/1990 | Niznick | |
| 4,976,739 A | 12/1990 | Duthie, Jr. | |
| 5,000,686 A | 3/1991 | Lazzara et al. | |
| 5,002,488 A * | 3/1991 | Homsy | 433/169 |
| 5,007,835 A | 4/1991 | Valen | |
| 5,061,181 A | 10/1991 | Niznick | |
| 5,062,800 A | 11/1991 | Niznick | |
| 5,071,350 A | 12/1991 | Niznick | |
| 5,074,790 A | 12/1991 | Bauer | |
| 5,076,788 A | 12/1991 | Niznick | |
| RE33,796 E | 1/1992 | Niznick | |
| 5,078,607 A | 1/1992 | Niznick | |
| 5,087,201 A | 2/1992 | Mondani et al. | |
| 5,194,000 A * | 3/1993 | Dury | 433/173 |
| 5,195,892 A | 3/1993 | Gersberg | |
| 5,226,766 A | 7/1993 | Lasner | |
| 5,230,590 A | 7/1993 | Bohannan et al. | |
| 5,328,371 A | 7/1994 | Hund et al. | |
| 5,343,391 A | 8/1994 | Mushabac | |
| 5,427,527 A | 6/1995 | Niznick et al. | |
| 5,433,606 A | 7/1995 | Niznick et al. | |
| 5,435,723 A | 7/1995 | O'Brien | |
| 5,439,381 A | 8/1995 | Cohen | |
| 5,484,286 A | 1/1996 | Hansson | |
| 5,527,183 A * | 6/1996 | O'Brien | 433/174 |
| 5,571,017 A | 11/1996 | Niznick | |
| 5,580,246 A | 12/1996 | Fried et al. | |
| 5,584,629 A | 12/1996 | Bailey et al. | |
| 5,601,429 A | 2/1997 | Blacklock | |
| 5,628,630 A | 5/1997 | Misch et al. | |
| 5,639,237 A | 6/1997 | Fontenot | |
| 5,642,996 A | 7/1997 | Mochida et al. | |
| 5,674,072 A | 10/1997 | Moser et al. | |
| 5,725,375 A | 3/1998 | Rogers | |
| 5,733,123 A | 3/1998 | Blacklock et al. | |
| 5,759,034 A * | 6/1998 | Daftary | 433/173 |
| 5,782,918 A | 7/1998 | Klardie et al. | |
| 5,795,160 A | 8/1998 | Hahn et al. | |
| 5,810,589 A * | 9/1998 | Michnick et al. | 433/169 |
| 5,810,590 A | 9/1998 | Fried et al. | |
| 5,816,812 A | 10/1998 | Kownacki et al. | |
| 5,823,776 A | 10/1998 | Duerr et al. | |
| 5,823,777 A | 10/1998 | Misch et al. | |
| 5,871,356 A | 2/1999 | Guedj | |
| 5,876,453 A | 3/1999 | Beaty | |
| 5,897,319 A | 4/1999 | Wagner et al. | |
| 5,915,968 A | 6/1999 | Kirsch et al. | |
| 5,938,444 A | 8/1999 | Hansson et al. | |
| 5,967,783 A | 10/1999 | Ura | |
| 6,068,479 A * | 5/2000 | Kwan | 433/173 |
| 6,095,817 A | 8/2000 | Wagner et al. | |
| 6,116,904 A | 9/2000 | Kirsch et al. | |
| 6,129,730 A | 10/2000 | Bono et al. | |
| 6,135,772 A | 10/2000 | Jones | |
| 6,149,432 A | 11/2000 | Shaw et al. | |
| 6,200,345 B1 | 3/2001 | Morgan | |
| 6,227,857 B1 * | 5/2001 | Morgan et al. | 433/173 |
| 6,227,859 B1 | 5/2001 | Sutter | |
| 6,273,722 B1 | 8/2001 | Phillips | |
| 6,287,117 B1 | 9/2001 | Niznick | |
| 6,312,259 B1 | 11/2001 | Kvarnstrom et al. | |
| 6,315,564 B1 | 11/2001 | Levisman | |
| 6,394,806 B1 | 5/2002 | Kumar | |
| 6,402,515 B1 | 6/2002 | Palti et al. | |
| 6,419,491 B1 | 7/2002 | Ricci et al. | |
| 6,481,760 B1 | 11/2002 | Noel et al. | |
| 6,547,564 B1 * | 4/2003 | Hansson | 433/174 |
| 6,626,671 B2 | 9/2003 | Klardie et al. | |
| 6,655,962 B1 | 12/2003 | Kennard | |
| 6,679,701 B1 | 1/2004 | Blacklock | |
| 6,726,481 B1 * | 4/2004 | Zickmann et al. | 433/173 |
| 6,726,689 B2 | 4/2004 | Jackson | |
| 6,733,291 B1 | 5/2004 | Hurson | |
| 6,733,503 B2 | 5/2004 | Layrolle et al. | |
| 6,769,913 B2 | 8/2004 | Hurson | |
| 6,913,465 B2 | 7/2005 | Howlett et al. | |
| 6,955,258 B2 | 10/2005 | Howlett et al. | |
| 7,014,464 B2 | 3/2006 | Niznick | |
| 7,104,797 B2 * | 9/2006 | Rassoli | 433/173 |
| 7,108,510 B2 | 9/2006 | Niznick | |
| 7,207,800 B1 * | 4/2007 | Kwan | 433/173 |
| 7,249,949 B2 | 7/2007 | Carter | |
| 7,273,373 B2 | 9/2007 | Horiuchi | |
| 7,281,925 B2 | 10/2007 | Hall | |
| 7,383,163 B2 | 6/2008 | Holberg | |
| 2001/0000748 A1 * | 5/2001 | Rogers et al. | 433/172 |
| 2002/0064758 A1 * | 5/2002 | Lee | 433/172 |
| 2002/0102518 A1 | 8/2002 | Mena | |
| 2002/0106612 A1 | 8/2002 | Back et al. | |
| 2002/0177106 A1 | 11/2002 | May et al. | |
| 2002/0182567 A1 | 12/2002 | Hurson et al. | |
| 2003/0064349 A1 * | 4/2003 | Simmons, Jr. | 433/173 |
| 2003/0124487 A1 * | 7/2003 | McDevitt | 433/173 |
| 2004/0006346 A1 * | 1/2004 | Holmen et al. | 606/73 |
| 2004/0063069 A1 * | 4/2004 | Lombardi | 433/173 |
| 2004/0121286 A1 | 6/2004 | Aravena et al. | |
| 2005/0053897 A1 * | 3/2005 | Wu | 433/173 |
| 2005/0106534 A1 | 5/2005 | Gahlert | |
| 2005/0147942 A1 | 7/2005 | Hall | |
| 2005/0214714 A1 | 9/2005 | Wohrle | |
| 2005/0244789 A1 * | 11/2005 | Crohin et al. | 433/173 |
| 2005/0260540 A1 | 11/2005 | Hall | |
| 2005/0266381 A1 * | 12/2005 | Abarno | 433/173 |
| 2005/0287497 A1 | 12/2005 | Carter | |
| 2006/0078847 A1 * | 4/2006 | Kwan | 433/174 |
| 2006/0172257 A1 | 8/2006 | Niznick | |
| 2006/0183078 A1 | 8/2006 | Niznick | |
| 2007/0099153 A1 | 5/2007 | Fromovich | |
| 2008/0014556 A1 | 1/2008 | Neumeyer | |
| 2008/0032264 A1 | 2/2008 | Hall | |
| 2008/0261175 A1 | 10/2008 | Hurson | |
| 2008/0261176 A1 | 10/2008 | Hurson | |
| 2009/0305192 A1 | 12/2009 | Hall | |

FOREIGN PATENT DOCUMENTS

| | | |
|---|---|---|
| DE | 10231743 B4 | 3/2005 |
| EP | 0475358 | 3/1992 |
| EP | 0707835 A1 | 10/1995 |
| EP | 0707835 B1 | 10/1995 |
| EP | 1 396 236 A | 3/2004 |
| EP | 1 624 826 A1 | 2/2006 |
| EP | 1 728 486 A | 12/2006 |
| EP | 1 624 826 A4 | 5/2007 |
| FR | 2600246 A1 | 12/1987 |
| JP | 61146757 | 7/1986 |
| JP | 8019555 A | 1/1996 |
| JP | 8-501962 | 3/1996 |
| JP | 3026125 | 4/1996 |
| JP | 10-052445 | 2/1998 |
| RU | 2190373 | 10/2002 |
| RU | 2202982 | 4/2003 |
| RU | 2202984 | 4/2003 |
| RU | 2204356 | 5/2003 |
| RU | 2262324 | 10/2005 |
| RU | 2273464 | 4/2006 |
| WO | WO 94/07428 | 4/1994 |
| WO | WO 94/09717 | 5/1994 |
| WO | WO 95/09583 | 4/1995 |
| WO | WO 97/05238 | 2/1997 |
| WO | WO 99/23971 | 5/1999 |
| WO | WO 00/00103 | 1/2000 |
| WO | WO 00/72775 | 12/2000 |
| WO | WO 00/72777 | 12/2000 |
| WO | WO 01/74412 | 10/2001 |

| | | |
|---|---|---|
| WO | WO 01/76653 | 10/2001 |
| WO | WO 02/45615 A1 | 6/2002 |
| WO | WO 03/030767 A | 4/2003 |
| WO | WO 03/034951 | 5/2003 |
| WO | WO 03/055405 | 7/2003 |
| WO | WO 03/055406 A1 | 7/2003 |
| WO | WO 03/063085 A1 | 7/2003 |
| WO | WO 03/103527 A2 | 12/2003 |
| WO | WO 2004/103202 | 12/2004 |
| WO | WO 2005/027771 A1 | 3/2005 |
| WO | WO 2005/072639 A1 | 8/2005 |
| WO | WO 2005/117742 A1 | 12/2005 |
| WO | WO 2006/081239 | 8/2006 |
| WO | WO 2006/138353 A2 | 12/2006 |

OTHER PUBLICATIONS

Niznick, Gerald A., DMD, MSD. "Proactive Nobel Active New Presentation," Implant Direct™, Oct. 16, 2007.

International Preliminary Report on Patentability for PCT Application No. PCT/IL2004/000438 filed May 23, 2004. Publication No. WO 04/103202 A1 published Dec. 2, 2004.

3.8D series Threaded Implant, dental implant sold before Sep. 27, 1999, Nobel Biocare.

Observation by AB Dental Devices Ltd. of Israeli Patent Application No. 156033 (PCT/IL2004/000438), a foreign counter-part of the present application, dated Sep. 7, 2005, including Appendix A, Appendix B and Appendix D.

Engineering Drawing of SPI 3.75/13 Implant, by Alpha Bio System.

Statement of Relevance by Ophir Fromovich.

International Search Report for Application No. EP04734484 filed May 23, 2004. Publication No. EP 1624826 A1, published Feb. 15, 2006.

Supplementary European Search Report for Application No. AP04734484 filed May 23, 2004. Publication No. EP 1624826 A4, published May 30, 2007.

* cited by examiner

FIG. 7B     FIG. 7A

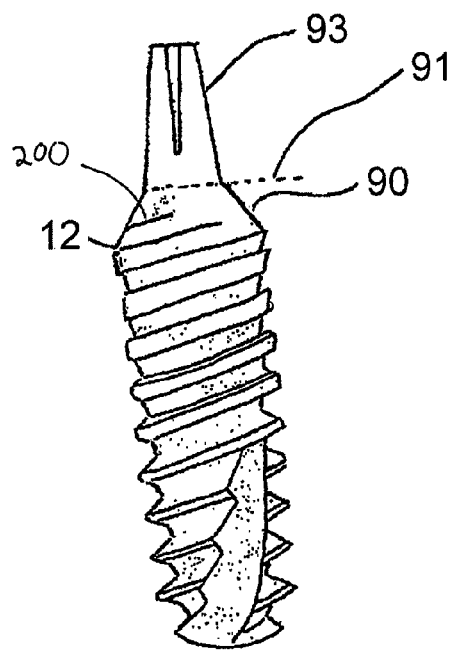
FIG. 12
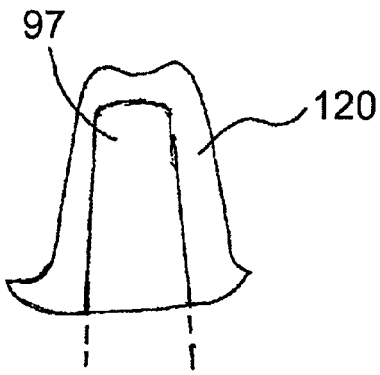
FIG. 14B
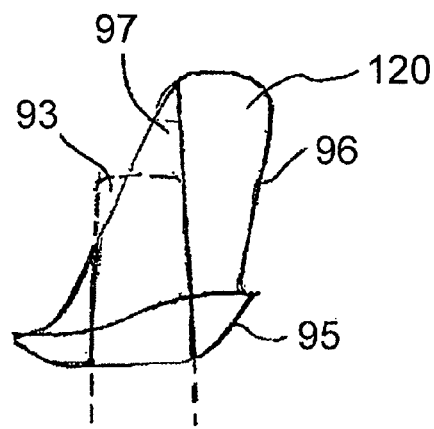
FIG. 14A
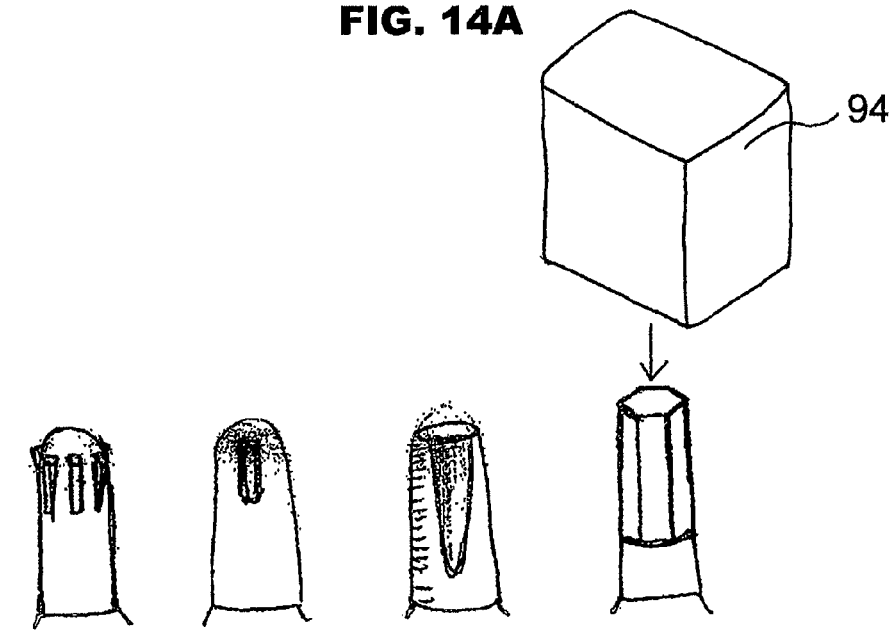
FIG. 13A   FIG. 13B   FIG. 13C   FIG. 13D

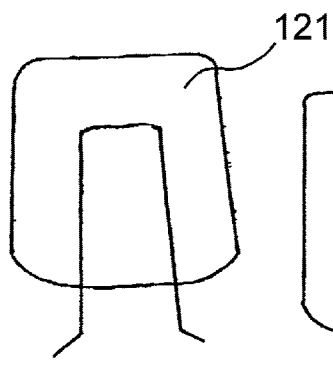
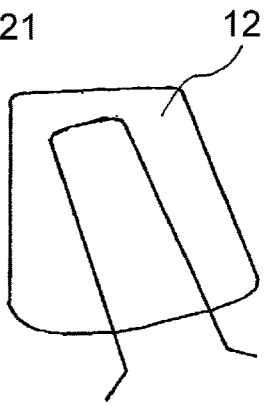
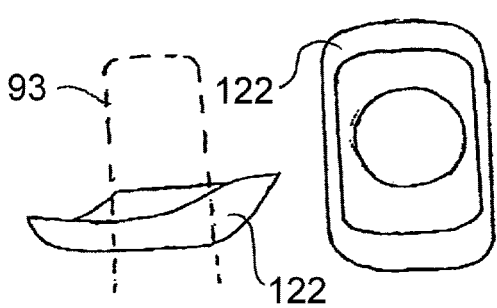
FIG. 15A  FIG. 15B  FIG. 16A  FIG. 16B
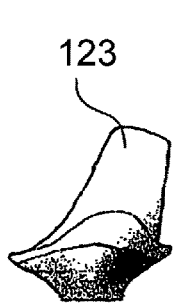
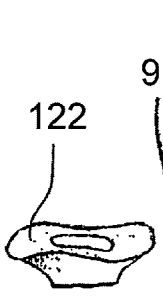
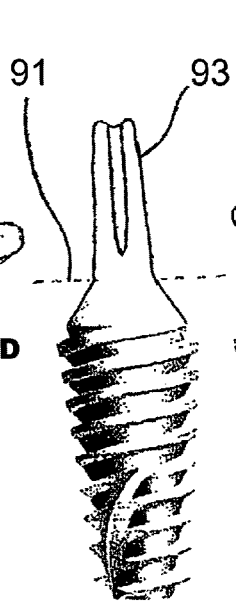
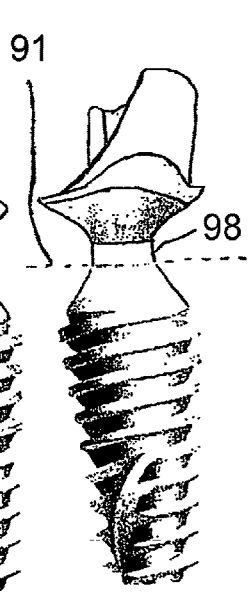
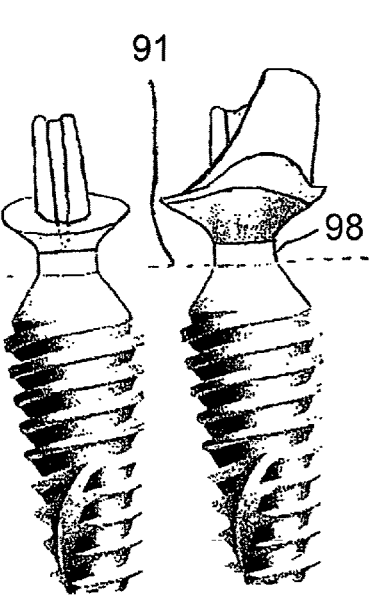
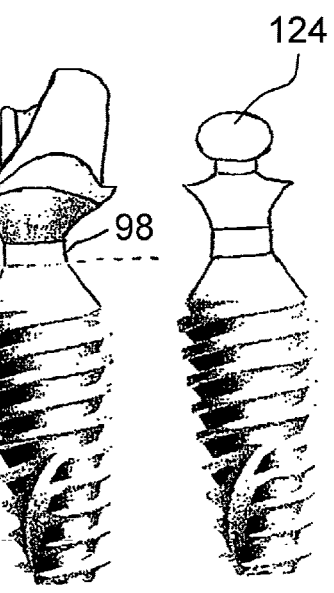
FIG. 17B  FIG. 17D  FIG. 17A  FIG. 17E  FIG. 17C  FIG. 17F

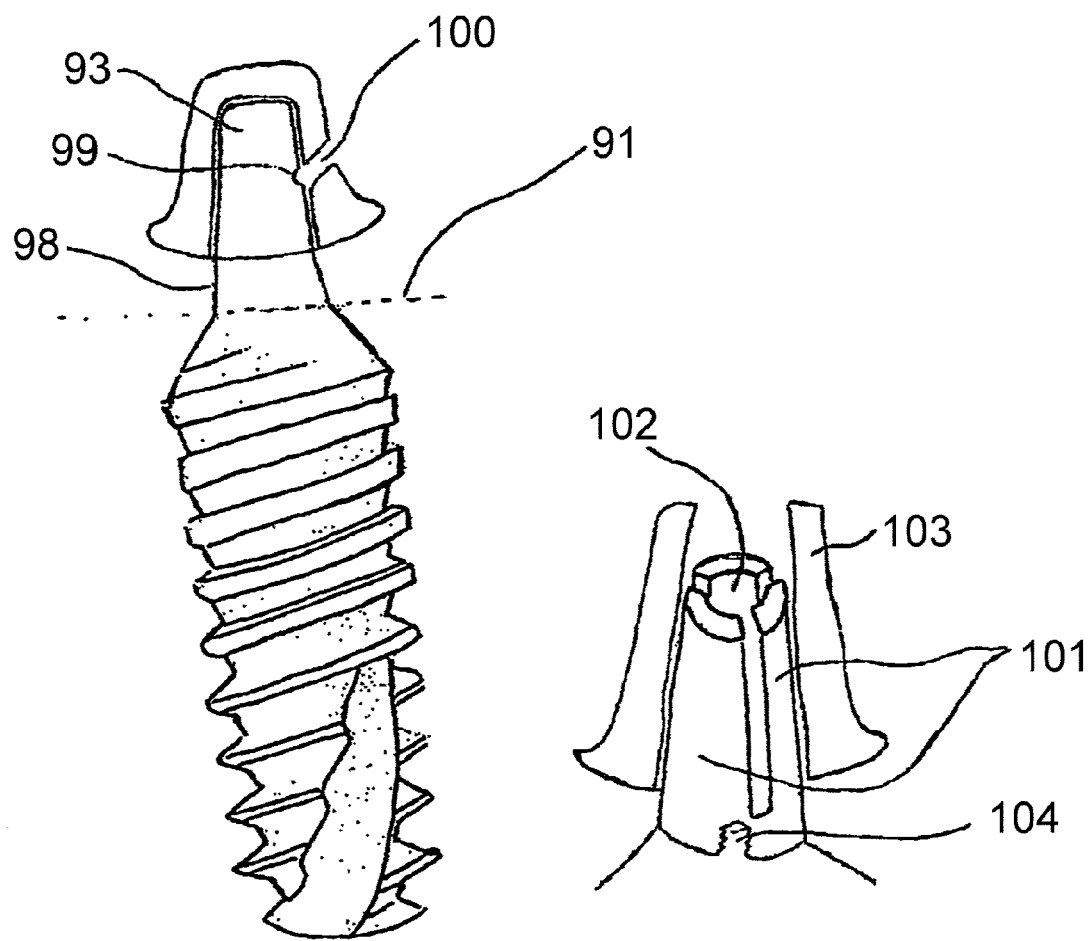
FIG. 18   FIG. 19

CONDENSING SKELETAL IMPLANT THAT FACILITATE INSERTIONS

RELATED APPLICATION INFORMATION

The present application is a continuation of U.S. patent application Ser. No. 10/558,260, filed Dec. 21, 2006, now U.S. Pat. No. 7,597,557, which is a continuation of International Application No. PCT/IL04/00438, filed May 23, 2004, which claims the priority benefit under 35 U.S.C. §119(a)-(d) to Israeli Patent Application No. 156033, filed May 21, 2003, the disclosures of which are incorporated by reference herein in their entirety.

BACKGROUND OF THE INVENTION

1. Field of the Invention

The disclosures herein relate generally to bone anchorage implants and more particularly to a screw form dental implant having a combination of features designed to produce bone condensation while insertion is easy.

2. Description of the Related Art

Many current screw-form dental implants are well designed for use in dense bone. For example, the implant disclosed in U.S. Pat. No. 5,897,319 has sharp cutting features at their apical ends that readily facilitate self-tapping into hard bone.

The osseous anatomy of the human jaw is complex. While the density of the bone in the anterior regions of the mandible and maxilla is high, the posterior regions, particularly in the maxilla, are of significantly lower density. The height of the bony ridge in the posterior maxilla can be greatly reduced in partially or totally edentulous patients. This can lead to the need for use of shorter dental implants or grafting procedures in order to increase the height of bone available for implant placement.

Dental implant stability in low-density bone, such as that found in the posterior regions of the mandible and maxilla and in regenerated bone, can be difficult to achieve. Compaction of low density bone, such as by the user of osteotomes, is commonly performed in order to enhance the stability of implants at the time of surgical placement.

Implants of various tapers and with various thread profiles are known in the art. For example, U.S. Pat. No. 5,427,527 describes a conical implant design that is placed into a cylindrical osteotomy site in order to induce bone compression at the coronal aspect of the implant, i.e., at its widest end.

A variety of thread profiles and patterns are known in the art. The most common design involves a symmetrical, V-shaped appearance such as that illustrated in U.S. Pat. No. 5,897,319. A variable thread profile is disclosed in U.S. Pat. Nos. 5,435,723 and 5,527,183 which is mathematically optimized for stress transfer under occlusal loads. U.S. Pat. Nos. 3,797,113 and 3,849,887 describe dental implants with external thread-like features having flat shelf facing the coronal end of the implant. U.S. Pat. No. 4,932,868 discloses a thread design with a flat surface disposed toward the apical end of the implant. This thread is not variable over different points of the implant and does not produce both cutting and compression actions as described herein. U.S. Pat. No. 5,007,835 discloses a screw-type dental implant with rounded threads for providing controlled radial osteocompressive force against the walls of a pre-tapped bone site. U.S. Pat. No. 5,628,630 discloses a method for designing dental implants to optimize and control stress transfer to surrounding bone including a thread design that changes from a sharp, highly angled profile at the apical end of the implant to a flat, nearly square profile at the coronal end, the goal being to control the surface area presented to occlusal forces. U.S. Pat. No. 6,402,515 describes a condensing implant with a gradually enlarged thread width to enhance stability in low density bone.

As an implant is designed to be more condensing its insertion becomes a more difficult. It is also more difficult to control the position of the implant since a condensing implant has a stronger tendency to slip into a region with the lowest bone density.

Therefore, what is needed is an implant that enhances stability in low density bone such as that formed in the posterior mandible and posterior maxilla but is easily inserted and can be used also in regular bone and in hard bone. It is also needed that the implant will keep its path of insertion and will not slip towards regions with low bone density.

SUMMARY OF THE INVENTION

This invention is of a skeletal screw that can be easily inserted inside bone and can be use in soft bone and hard bone. The following description will focus on dental implants but all the details can be implemented also in orthopedics for other regions of the body. One embodiment, accordingly, provides a dental implant that is particularly suited for use in lower density bone but can be used also in hard bone. To this end, a dental implant having a variable profile thread includes a body having a coronal end and an apical end. The body includes a tapered core adjacent the apical end. The core is not forming a straight line in cross section. The core is like a circular osteotomes so the difference between the diameter of the core just coronally to a thread and the diameter of the core just apically to this thread is smaller compared to a regular tapered implant with the same angle of tapering. A variable width helical thread extends along the tapered core. The thread has an apical side, a coronal side, a lateral edge and a base touching the core of the implant. A height defined between the lateral edge and the coronal edge. The width is defined by the length of the lateral edge. The variable width is expanded in the direction of the coronal end. As a result, the least width of the thread is adjacent the apical end and the greatest width of the thread is adjacent the coronal end. The variable height is expanded in the direction of the apical end. As a result, the least height of the thread is adjacent the coronal end and the greatest height of the thread is adjacent the apical end. The implant has preferably two threads running along the implant. This implant has two cones, one for the outer surface of the threads and the second for the inner surface of the threads meaning the core. The angle of the first cone is smaller than the angle of the second cone. The implant also has a spiral bone tap and coronal region with a smaller tapering.

A principal advantage of this embodiment is that a dental implant is provided that addresses the problems described above. It has a unique combination of implant body and thread profile that enhances stability in low-density bone but the insertion is easily done and the direction of the implant is dictated by the high apical threads that prevent slipping of the implant.

The coronal region of the implant is preferably converging coronally. This region is to be placed below the bone level and the bone is covering this region because the implant is designed to allow insertion with a small diameter drill and to allow elastic expansion of the cortical bone. The presence of bone above the implant supports the gums to achieve an esthetic result. In some preferred embodiments the implant is a one-piece implant preventing bone resorbtion. There are also provided several novel prosthetic systems that fit the new implant but can be also used for other implants.

Thus according to the teaching of the present invention there is provided a dental implant comprising: a body; a coronal end of the body; an apical end of the body. The apical end having a tapered core with helical thread extending along the tapered core, the apical end includes at least one region having coronal thread which is coronal to a coronal core segment which is coronal to an apical thread which is coronal to an apical core segment, the region is designed so when the most apical aspect of the border of the coronal core segment is continued by an imaginary straight line apically through the apical thread the line will be inside the apical core segment.

According to a further feature of the present invention, the core having a variable width helical thread extending along the core, the thread having an apical side, a coronal side and a width defined between the apical and coronal sides, and the variable width being progressively expanded substantially along the entire threaded region of the implant in the direction of the coronal end, so that a least width of the thread adjacent the apical end and a greatest width of the thread is adjacent the coronal end.

According to a further feature of the present invention, the apical end includes at least one region having a tapered variable profile helical thread extending along the core, the thread having an apical side, a coronal side, a lateral edge connecting the apical side and the coronal side, a base touching the core, a height defined between the lateral edge and the base, a variable length of the lateral edge being progressively expanded substantially along the region of the apical end in the direction of the coronal end, so that a least length of the lateral edge of the thread is adjacent the apical end and a greatest length of the lateral edge of the thread is adjacent the coronal end, and a variable height being progressively expanded substantially along the entire threaded region of the implant in the direction of the apical end, so that a least height of the thread is adjacent the coronal end and a greatest width of the thread is adjacent the apical end.

According to a further feature of the present invention, the apical side of the thread includes a flat shelf and the width of the thread is further defined by a circumferential face extending between the apical side and the coronal side. According to a further feature of the present invention, the circumferential face has a flat face substantially perpendicular to the flat shelf and wherein the flat face has a width that progressively expands from the apical end toward the coronal end. According to a further feature of the present invention, the flat face narrows at the apical end and becomes sharp and thin.

According to a further feature of the present invention, the apical end includes a rounded region.

According to a further feature of the present invention, the thread is self-tapping adjacent the apical end.

According to a further feature of the present invention, the self-tapping thread is spaced from the rounded region.

According to a further feature of the present invention, the borders of the core segments are forming parallel lines.

According to a further feature of the present invention, the borders of the core segments are not straight lines.

According to a further feature of the present invention, wherein the lateral edge is parallel to the long axis of the implant.

According to a further feature of the present invention, the body of the implant is tapered and wherein the thread adjacent the apical end is self-tapping and adapted to cut bone.

According to a further feature of the present invention, the apical end includes a spiral tap, the spiral tap extends from one side of the implant to the opposite side along more than a third of the length of the implant.

According to a further feature of the present invention, the most coronal aspect of the coronal end is tapered coronally forming narrower coronal edge.

There is also provided according to the teachings of the present invention a dental implant comprising: a body; a coronal end of the body; an apical end of the body; the apical end having a core, the apical end includes at least one region having a tapered variable profile helical thread extending along the core, the thread having an apical side, a coronal side, a lateral edge connecting the apical side and the coronal side, a base touching the core, a height defined between the lateral edge and the base, a variable length of the lateral edge being progressively expanded substantially along the region of the apical end in the direction of the coronal end, so that a least length of the lateral edge of the thread is adjacent the apical end and a greatest length of the lateral edge of the thread is adjacent the coronal end, and a variable height being progressively expanded substantially along the entire threaded region of the implant in the direction of the apical end, so that a least height of the thread is adjacent the coronal end and a greatest width of the thread is adjacent the apical end. According to a further feature of the present invention, the apical side of the thread includes a flat shelf and the width of the thread is further defined by a circumferential face extending between the apical side and the coronal side.

According to a further feature of the present invention, the circumferential face has a flat face substantially perpendicular to the flat shelf and wherein the flat face has a width that progressively expands from the apical end toward the coronal end. According to a further feature of the present invention, the flat face narrows at the apical end and becomes sharp and thin.

According to a further feature of the present invention, the apical end includes a rounded region.

According to a further feature of the present invention, the thread is self-tapping adjacent eh apical end.

According to a further feature of the present invention, the self-tapping thread is spaced from the rounded region.

According to a further feature of the present invention, the lateral edge is parallel to the long axis of the implant.

According to a further feature of the present invention, the core is tapered.

According to a further feature of the present invention, the thread adjacent the apical end is self-tapping and adapted to cut bone.

According to a further feature of the present invention, the apical end includes a spiral tap, the spiral tap extends from one side of the implant to the opposite side along more than a third of the length of the implant.

According to a further feature of the present invention, the most coronal aspect of the coronal end is tapered coronally forming narrower coronal edge.

There is also provided according to the teachings of the present invention a dental implant comprising: a body; a coronal end of the body; an apical end of the body; the apical end having a tapered core with helical tapered thread extending along the tapered core, the apical end includes at least one region where the angle of the tapered core is larger than the angle of the helical tapered thread.

According to a further feature of the present invention, the apical end having coronal thread which is coronal to a coronal core segment which is coronal to an apical thread which is coronal to an apical core segment, the region is designed so when the most apical aspect of the border of the coronal core segment is continued by an imaginary straight line apically through the apical thread the line will be inside the apical core segment.

According to a further feature of the present invention, the core having a variable width helical thread extending along at least one segment of the core, the thread having an apical side, a coronal side and a width defined between the apical and coronal sides, and the variable width being progressively expanded substantially along the segment of the implant in the direction of the coronal end, so that a least width of the thread adjacent the apical end and a greatest width of the thread is adjacent the coronal end.

According to a further feature of the present invention, the apical end includes at least one segment having a tapered variable profile helical thread extending along the core, the thread having an apical side, a coronal side, a lateral edge connecting the apical side and the coronal side, a base touching the core, a height defined between the lateral edge and the base, a variable length of the lateral edge being progressively expanded substantially along the segment of the apical end in the direction of the coronal end, so that a least length of the lateral edge of the thread is adjacent the apical end and a greatest length of the lateral edge of the thread is adjacent the coronal end, and a variable height being progressively expanded substantially along the segment of the implant in the direction of the apical end, so that a least height of the thread is adjacent the coronal end and a greatest height of the thread is adjacent the apical end.

According to a further feature of the present invention, the apical side of the thread includes a flat shelf and the width of the thread is further defined by a circumferential face extending between the apical side and the coronal side. According to a further feature of the present invention, the circumferential face has a flat face substantially perpendicular to the flat shelf and wherein the flat face has a width that progressively expands from the apical end toward the coronal end. According to a further feature of the present invention, the flat face narrows at the apical end and becomes sharp and thin.

According to a further feature of the present invention, the apical end includes a rounded region.

According to a further feature of the present invention, the thread adjacent the apical end is self-tapping.

According to a further feature of the present invention, the self-tapping thread is spaced from the rounded region.

According to a further feature of the present invention, the borders of the core segments are forming straight parallel lines.

According to a further feature of the present invention, the borders of the core segments are not straight lines.

According to a further feature of the present invention, the lateral edge is parallel to the long axis of the implant.

According to a further feature of the present invention, the body of the implant is tapered and wherein the thread adjacent the apical end is self-tapping and adapted to cut bone.

According to a further feature of the present invention, the apical end includes a spiral tap, the spiral tap extends from one side of the implant to the opposite side along more than a third of the length of the implant.

According to a further feature of the present invention, the most coronal aspect of the coronal end is tapered coronally forming narrower coronal edge.

According to a further feature of the present invention, the coronally tapered aspect has a surface designed to be in contact with bone.

According to a further feature of the present invention, the coronally tapered aspect is designed to allow elastic expansion of the bone while inserting the wider area of the coronally tapered aspect inside the bone and after insertion of the narrow area of the coronally tapered aspect the bone relapses to cover the coronally tapered aspect. According to a further feature of the present invention, the implant has more than one thread.

According to a further feature of the present invention, the threads reach the coronally tapered aspect.

According to a further feature of the present invention, the implant has threads on the coronally tapered region.

According to a further feature of the present invention, the implant includes a protruding element configured to protrude through the gums to allow the connection to a dental prosthesis.

According to a further feature of the present invention, the protruding element and the implant are one piece.

According to a further feature of the present invention, the protruding element includes at least one region with an anti-rotational element.

According to a further feature of the present invention, the protruding element is tapered coronally.

According to a further feature of the present invention, the protruding element is designed to get a wider collar that mimics the emergence profile of a natural tooth.

According to a further feature of the present invention, the protruding element is configured to be attached to an abutment from the side.

BRIEF DESCRIPTION OF THE DRAWINGS

FIG. 12 is a side elevation view illustrating another embodiment of a one-piece dental implant with a coronally tapered coronal region.

FIG. 13A-D are side elevations views illustrating different types of anti-rotational element that can be used with the implant of FIG. 12.

FIG. 14A is a side elevation view illustrating a full anatomical angled abutment to be fitted over the implant of FIG. 12.

FIG. 14B is a side elevation view illustrating a full anatomical straight abutment to be fitted over the implant of FIG. 12.

FIG. 15A is a side elevation view illustrating a bulky straight abutment to be fitted over the implant of FIG. 12.

FIG. 15B is a side elevation view illustrating a bulky angled abutment to be fitted over the implant of FIG. 12.

FIG. 16A is a side elevation view illustrating a gingival antomic collar to be fitted over the implant of FIG. 12.

FIG. 16B is a top view illustrating the collar of FIG. 16A.

FIG. 17A is a perspective view illustrating another embodiment of a one-piece dental implant with a coronally tapered coronal region.

FIG. 17B is a perspective view illustrating another embodiment an abutment to be fitted over the implant of FIG. 17A.

FIG. 17C is a perspective view of the implant of FIG. 17A with the abutment of FIG. 17B.

FIG. 17D is a perspective view illustrating another embodiment a collar to be fitted over the implant of FIG. 17A.

FIG. 17E is a perspective view of the implant of FIG. 17A with the collar of FIG. 17D.

FIG. 17F is a perspective view of the implant of FIG. 17A with a ball attachment.

FIG. 18 is a side elevation view illustrating an abutment with locking mechanism.

FIG. 19 is a side elevation view illustrating another embodiment of an implant with locking mechanism to the abutment.

DETAILED DESCRIPTION OF THE PREFERRED EMBODIMENT

Figure illustrates an embodiment of the novel tapered condensing dental implant. There are five elements in a dental implant that influence the condensation, insertion and stabilization of the implant. 1) The core of the implant 40. 2) The Threads 41. 3) The most apical region 42 which touches the bone first. 4) The bone tap 43. 5) The most coronal region 44 which engages the cortical bone and the sometimes also the gums.

In order to have good stabilization in low density bone it is recommended to use small diameter drill and tapered implant. AS the diameter of the drill is smaller and the implant is more tapered the bone is more preserved and more condensed resulting in improved stabilization, but the insertion is more difficult. In this case controlling the exact path of insertion of the implant becomes also more difficult sine the implant has a tendency to slip towards the region with the lowest density. In order to use a small diameter drill and an implant with significant tapered configuration all five elements of the implant have to be designed to allow an easy insertion and good control on the final position of the implant.

Figure 2:
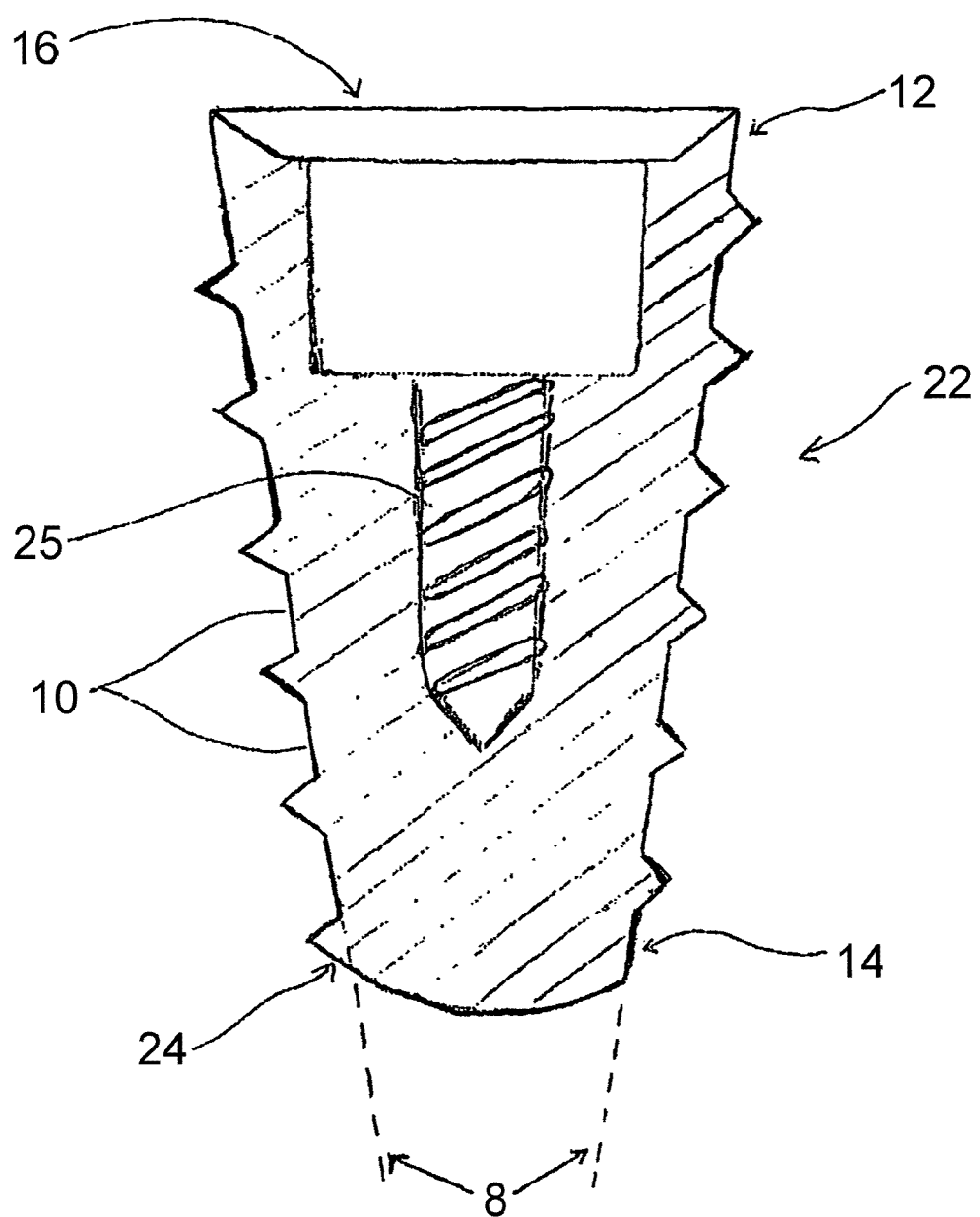
FIG. 2 is a cross-sectional view illustrating a regular tapered dental.

In order to clarify the novelty of the new implant it will be compared to a regular tapered implant like the implant illustrated in FIG. 2. The implant has a coronal end 12 and an apical end 14. The implant has five distinct regions. At the most coronal aspect is an implant-prosthetic interface region 16. Moving from the coronal to the apical ends the implant can have an optional mechanical stop region (not shown), an optional cylindrical region (not shown), a tapered region 22, and a bone cutting end region 24 which is self drilling and self tapping. An internal threaded portion 25 is provided for the attachment of prosthetic components.

The interface region 16 provides mechanical interlock between the implant and the prosthetic components (not shown) attached to the implant. Interface region 16 also provides a means of applying torque to the implant and thus driving the implant into the selected site. The interface region 16 can be any of a number of known interfaces, including external splines or polygons, or internal geometric shapes such as polygons or Morse tapers.

The optional mechanical stop region can be sharply tapered so that when the implant is screwed into a prepared osteotomy, the stop limits inadvertently placing the implant too deeply.

Figure 3:
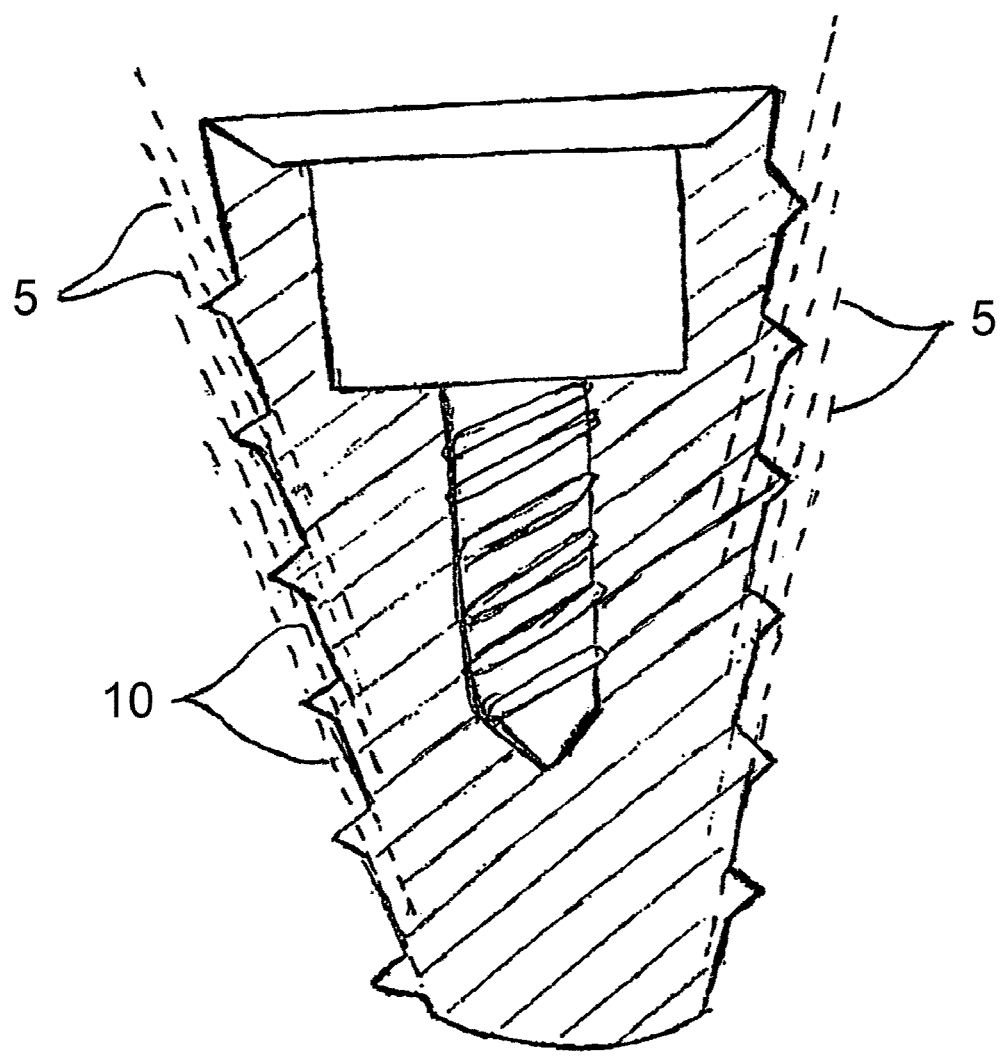
FIG. 3 is a cross-sectional view illustrating an embodiment of a dental implant of the present invention having a gradual condensing core.

The shape of the core can be seen in segments 10 in the spaces between the threads in cross-sectional view FIG. 2. When connecting the outer border of these segments in all the tapered implants known in the field straight lines 8 are formed as illustrated in FIG. 2. This configuration causes strong resistance for insertion. In the present invention when connecting the outer border of these segments, imaginary segment lines 5 are formed as illustrated in FIG. 3. This configuration enables gradual condensation since the diameter of the lower aspect of each segment is close to the upper diameter of the previous apical segment. This gradual condensation of the core allow for easy insertion of the implant without loosing the final condensation and stability since the difference in the diameter between two adjacent core segments is the same, allowing it to act as if it is a regular implant like the implant in FIG. 2. However, the final condensation is even greater since the core condenses the bone with a more tapered core. The angles of the imaginary segment lines 5 of the core segments in FIG. 3 of the novel implant are greater than the angles of the lines 8 of the regular tapered implant of FIG. 2. Therefore, the implant of FIG. 3 has an overall shape that is tapered like the implant of FIG. 2 (the angle between lines 8) but condenses the bone like a more tapered implant (the angle between imaginary segment lines 5) and allows gradual condensation to facilitate insertion.

Figure 4:
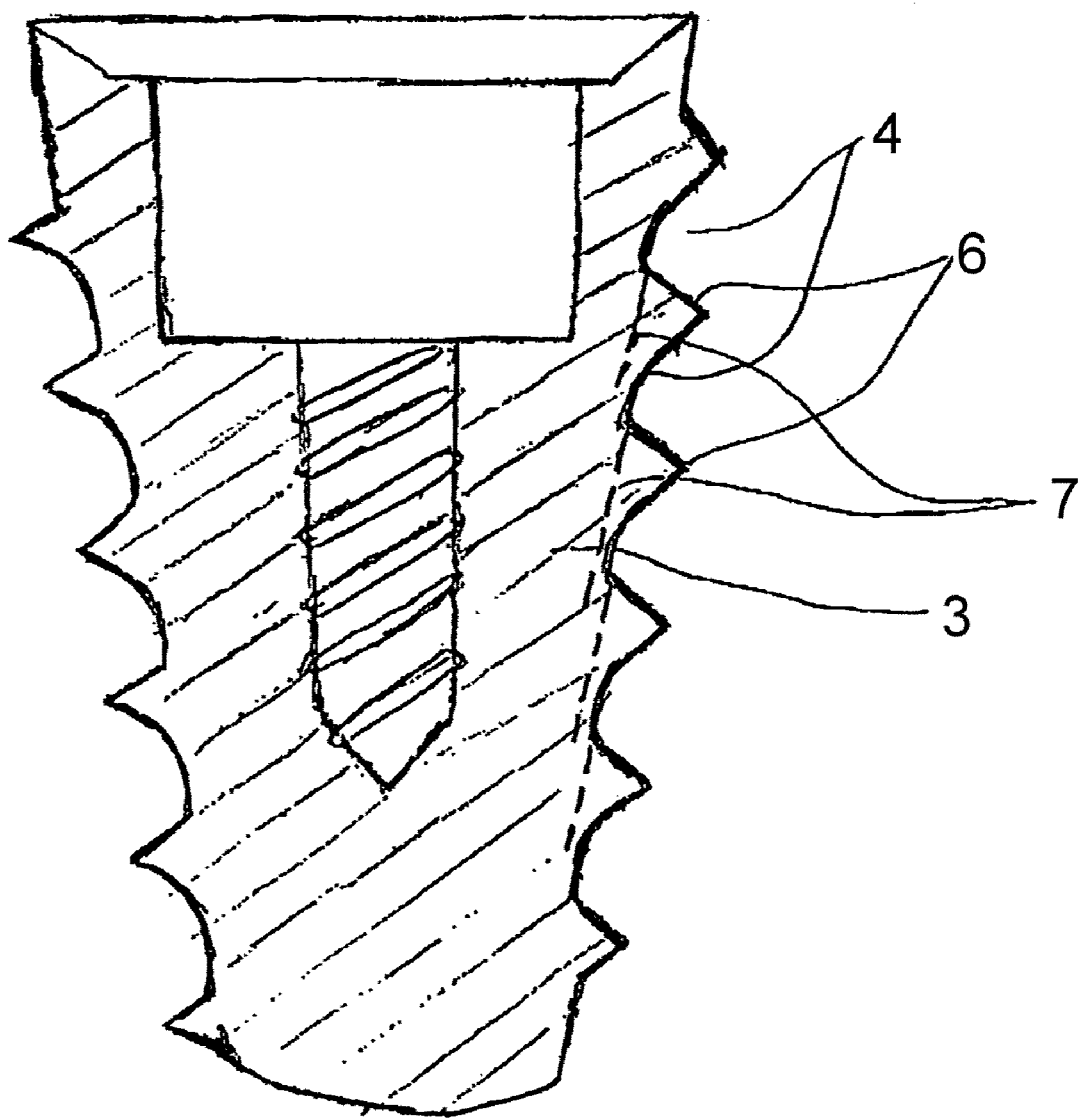
FIG. 4 is a cross-sectional view illustrating an embodiment of a dental implant of the present invention with rounded borders of the core segments.

The imaginary segment lines 5 of FIG. 3 which are the continuation of the border of the core segments 10 are parallel and straight. The imaginary segment lines 5 are at an angle X relative to a longitudinal axis 9 of the dental implant. An imaginary core line 30 of FIG. 6 runs along the points where the coronal sides of at least some core segment meets the thread. The imaginary core line is at an angle Y relative to the longitudinal axis, which in some embodiment is a smaller angle than angle X. This is one preferred embodiment, but there are other shapes of the border of the core segments that will function similarly. We can examine this character of the core of the implant for example in FIG. 4 that illustrates a dental implant with a rounded border of the core segment. By continuing the border of a core segment 4 positioned coronaly to a thread 6 through the thread 6 by imaginary line 7. If the imaginary line enters inside the core segment 3 apically to the thread 6 it will function the same to allow gradual condensation, but the condensation is strong only on the apical region of the core border. The preferred embodiment with straight border lines FIG. 3 allows for gradual condensation along all the border so the insertion is smoother.

The threads preferably have a variable profile. The tapered region 22 of FIG. 5 has on its external surfaces a thread 28 of novel profile. The external thread 28 includes a progressively changing profile. At the apical end 14, the thread 28 is sharp narrow and high in order to facilitate cutting and self-tapping into bone. As the thread 28 progresses towards the implant coronal end 12, its tip becomes increasingly broad or wider in the apical -coronal direction and increasingly lower in the horizontal direction in cross-sectional profile. The increasing breadth of thread 28 facilitates compression of low-density bone previously tapped by the sharp apical thread profile. Bone compression increases the stability of the implant. The decreasing height allows easy insertion and dictates that the implant will keep its first direction while it is inserted. As the thread 28 progresses from coronal to apical ends, 12 and 14 respectively, of the implant, the thread 28 becomes sharper, thinner and higher. Thread 28 is profiled so that a path cut or created in the bone is gradually broadened by compression due to the progressively broader thread 28. In this preferred embodiment the threads are tapered and the core is more tapered resulting in higher threads at the apical region. This configuration is suitable also for very dense bone. In highly dense bone sometimes the blood supply is compromised resulting in implant failure. The novel implant of FIG. 5 has high and spaced threads leaving spaces between them after insertion to hard bone following drilling with a wide drill. These spaces will promote blood vessels proliferation and bone regeneration.

Figure 6:
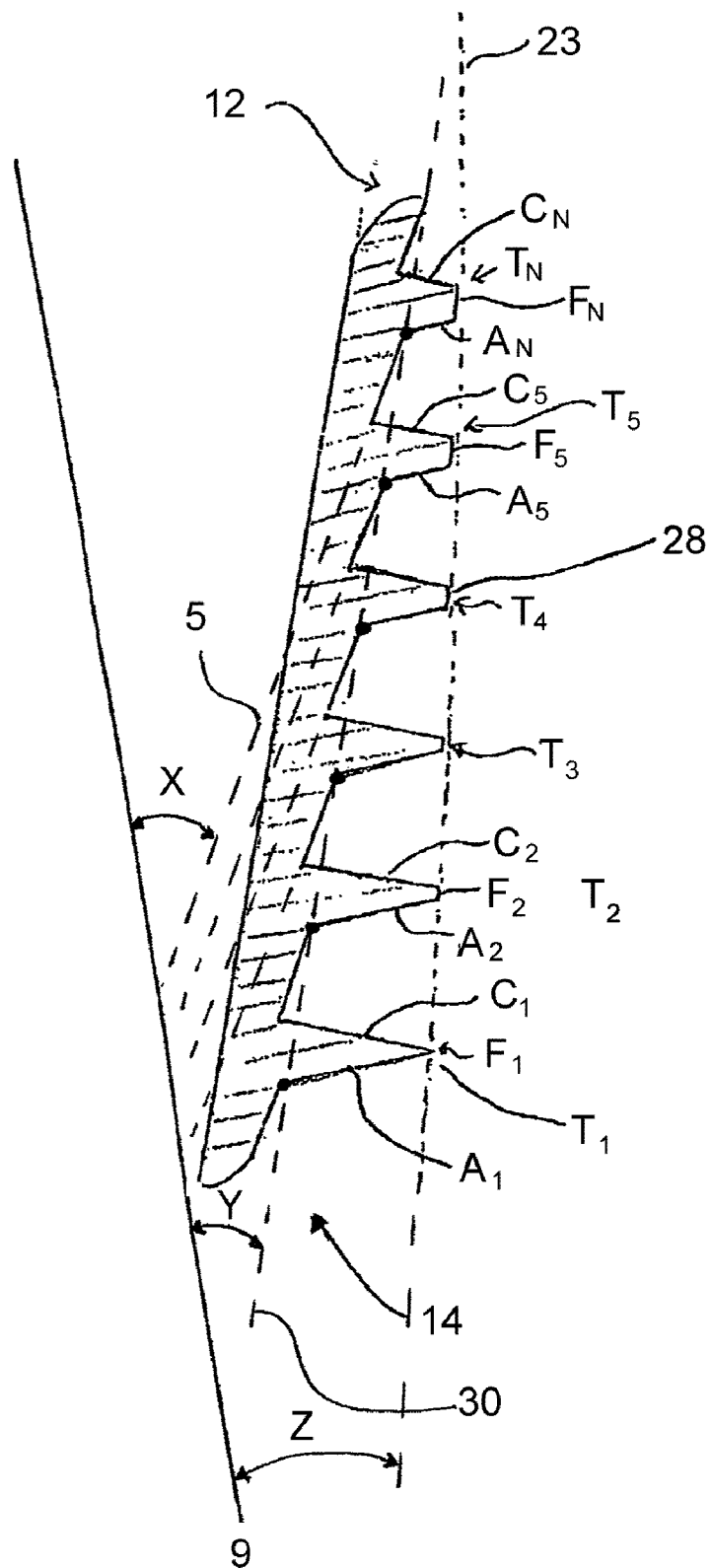
FIG. 6 is a partial section taken from FIG. 5.

FIG. 6 more particularly illustrates the variable profile thread 28. Each turn T of thread 28 is of a different profile from each other turn T of thread 28. For example, implant includes a plurality of turns $T_1$, $T_2$, $T_3$, ... $T_N$. Each turn T includes an apical side A and a coronal side C and flat face F connecting A and C. The length of F varies by being continuously expanded in the direction of the coronal end 12. The length of A and C varies by being continuously expanded in the direction of the apical end 14.

Figure 5:
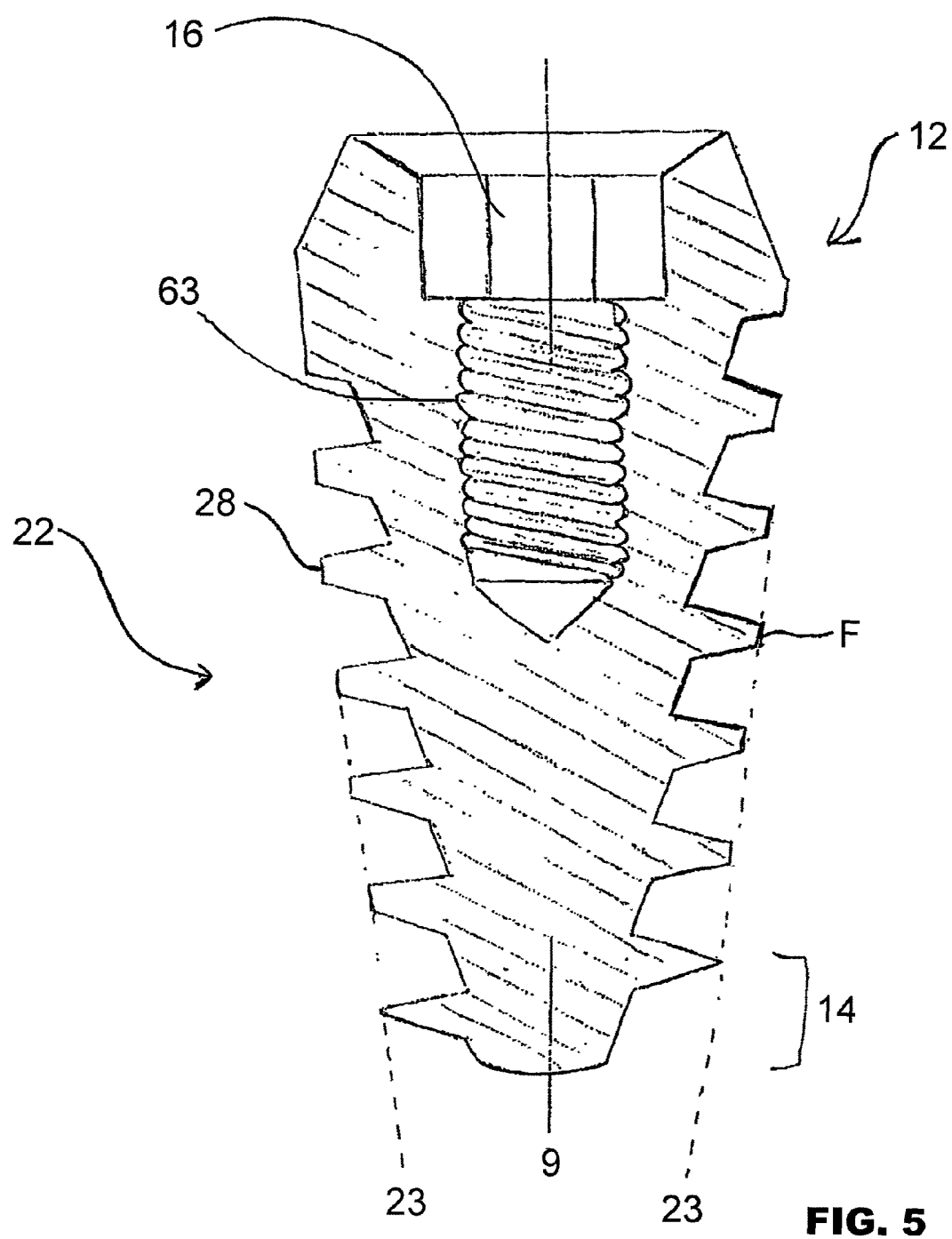
FIG. 5 is a cross-sectional view of the novel implant.

As such, a first turn $T_1$, includes an apical side $A_1$, a coronal side $C_1$, and $F_1$. A second turn $T_2$ includes an apical side $A_2$, a coronal side $C_2$, and a $F_2$. The same pattern is repeated for turns $T_1$, $T_2$, $T_3$, ... $T_N$. so that a least length $F_1$, of the thread 28 is adjacent the apical end 14, and a greatest length $F_N$ is adjacent the coronal end 12. The least length $A_N$, of the thread 28 is adjacent the coronal end 12, and a greatest length $A_1$ is adjacent the apical end 14. The least length $C_N$, of the thread 28 is adjacent the coronal end 12, and a greatest length $C_1$ is adjacent the apical end 14. The apical side of the thread can be a flat shelf perpendicular to the long axis 9 of the implant or with a non 90 degrees angle to the long axis of the implant as illustrated in FIGS. 5 and 6. In addition, the external thread 28 may have a flat shelf and rounded tip, which are most pronounced at the thread's coronal end 12. The flat shelf provides support against implant micro-motion imposed by axial loads, particularly important in low-density bone. The tip of the thread F can be flat or rounded. The angle of the each thread segment meaning the angle between A and C of FIG. 6 is about 60 degree. To allow cutting of the bone a more sharp angle is preferred at 30-40 degree preferably at 35 degree. Preferably all the threads have the same angle between A and C. In another preferred embodiment the angle between A and C is gradually increased coronally to get more condensation for soft bone or gradually decreased coronally for hard bone.

Figure 1:
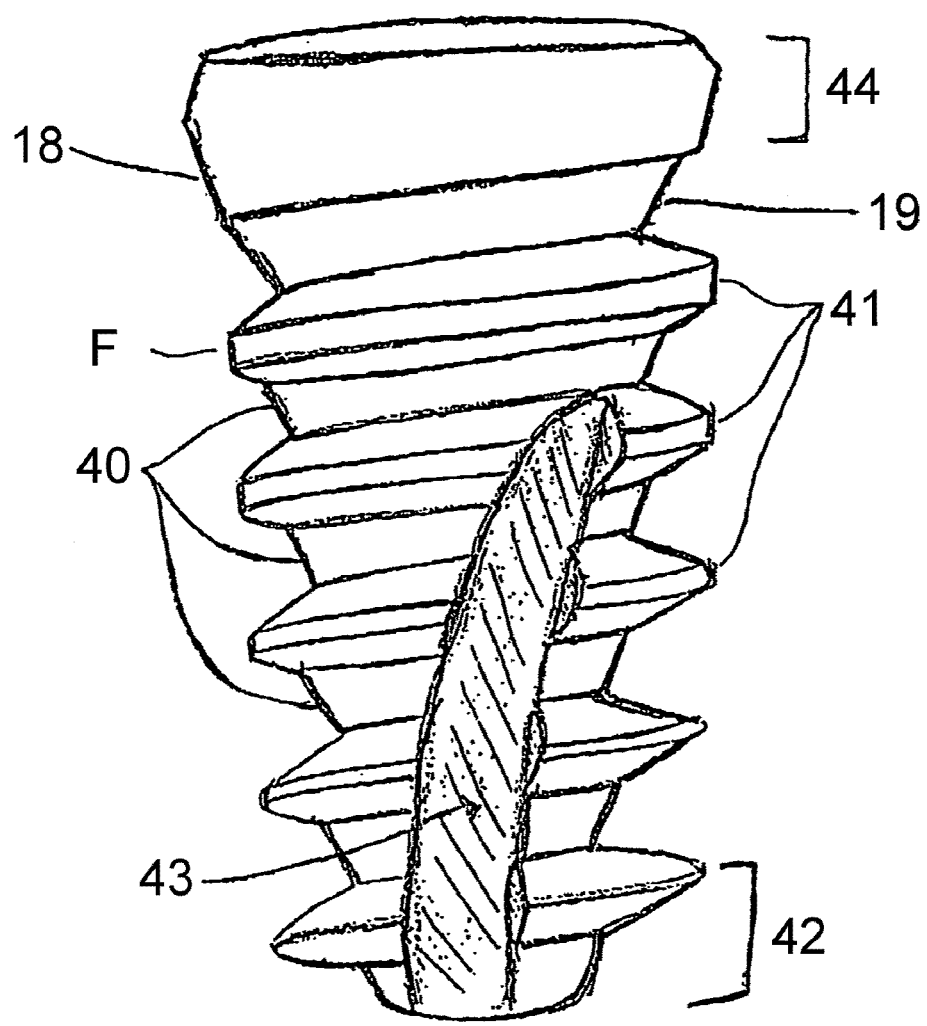
FIG. 1 is a side elevation view illustrating an embodiment of a dental implant of the present invention.

In the preferred embodiments of FIGS. 1,5,6, a circumferential face F is included on some turns of thread 28. The face F is preferably flat and is not included on the self-tapping portion of the thread 28, adjacent the apical end 14, but is provided as each turn progressively widens toward the coronal end 12. The face F preferably parallel to the long axis 9 of the implant but it can be also angled.

The threads are also tapered. The imaginary thread lines 23 of FIGS. 5 and 6 connecting the tips of the threads are not parallel to the longitudinal axis 9 of the implant. These imaginary thread lines 23 are at an angle Z relative to the longitudinal axis 9, as illustrated in FIG. 6. In some embodiments, angle Z is smaller than angle Y and angle Y is smaller than angle X. The threads are tapered and at the same time become higher apically because the core of the implant is more tapered than the threads. The fact that the width of the apical region of the implant is smaller than the coronal region allows the use of a small drill therefore preserving the bone. The sharp apical threads enter the small hole in the bone and start cutting the bone. The next thread is wider in the coronal apical direction and the implant is wider causing compression of the bone but since the height of the thread is less than the previous thread the thread stays in the path created in the bone by the previous thread therefore preventing slipping of the implant to a region with even lower density bone. The fact that the height of the threads become smaller as going coronally allows for gradual compression of the bone and facilitate insertion. The combination of a gradual tapered compressing core as described above with a gradual compressing tapered thread as described here is the preferred embodiment. The implant preferably has more than one thread. An implant with double thread each thread with a double step allows insertion in half the turns needed for an implant with one thread while keeping the outer surface and the stability of the implant. The implant can have more than two threads.

The most apical region of the implant can have two preferred configurations. One is smooth round design, this design is suitable for cases that the implant is near the Schneiderian membrane of the maxillary sinus or near the mandibular nerve in order to prevent damage to these delicate tissues. In this design the threads start with a distance from the apical end. The second design of the most apical region illustrated in FIGS. 7A and B is to have sharp blades that cut the bone and allow easy insertion. There are several variations for the shape of the blades, which are well known in the dental implant field. Implants with this apical design are called self drilling implants.

Figure 7:
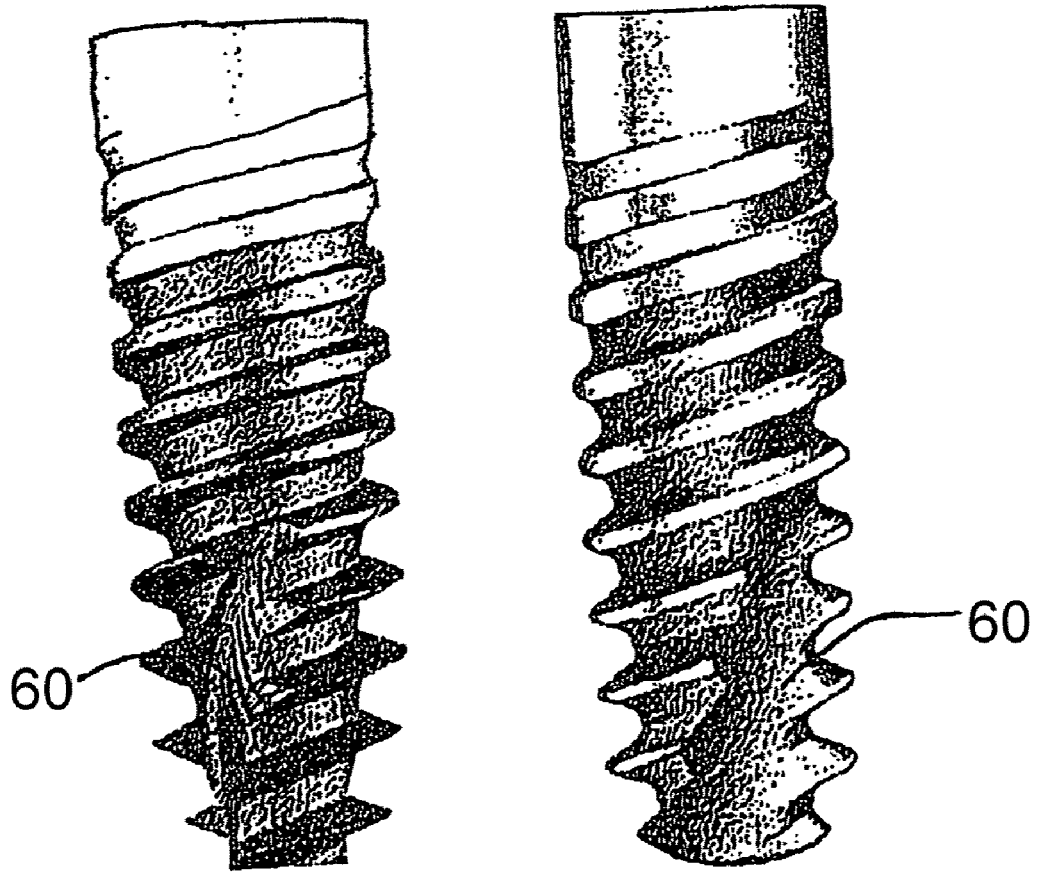
FIG. 7A is a side elevation view illustrating another embodiment of a dental implant of the present invention.
FIG. 7B is a side elevation view illustrating another side of the implant of FIG. 7A

The bone tap of the implant influence the insertion. The presence of a bone tap allows the insertion of the implant without previous taping of the bone. Implants with a tap are called self tapping implants. The tap can be straight or oblique or spiral. The preferred design is the spiral bone tap to facilitate insertion. The tap 60 as illustrated in FIG. 7 is long and going through more than a third of the length of the implant crossing several threads. Preferably the tap extends along more than half of the implant. The tap is not straight but surrounding the implant. The tap starts at on side of the implant FIG. 7A and extends to the other side FIG. 7B. The whole tap can't be seen from one place. This design of the tap facilitate insertion so when the implant is inserted only part of one thread is cutting the bone therefore the resistance for insertion is lower. This configuration together with the design of the thread as described above also dictates that the implant will stay in its original path of insertion by forcing the next thread to go into the slot in the bone prepared by the previous thread. This feature is enhanced by the presence of a double thread. The implant can have more than one tap preferably two.

The most coronal region of the implant also influences the insertion and stabilization of the implant. This region includes the interface region. There are several types of interfaces like splines whereas, the interface region 16' of a single-stage embodiment of FIG. 5, may optionally include a socket having a plurality of sides, e.g. a hex socket. Also, the embodiment of FIG. 1 does not include a sharply tapered mechanical stop as but instead includes a gradually tapered portion 18. The gradually tapered portion 18 allows for more freedom in placement depth to adjust the distance that the trans-gingival collar protrudes from the bone. However, an alternate single-stage embodiment can include a coronal region 44 including a second angled portion 19 which acts as a stop.

Figure 8:
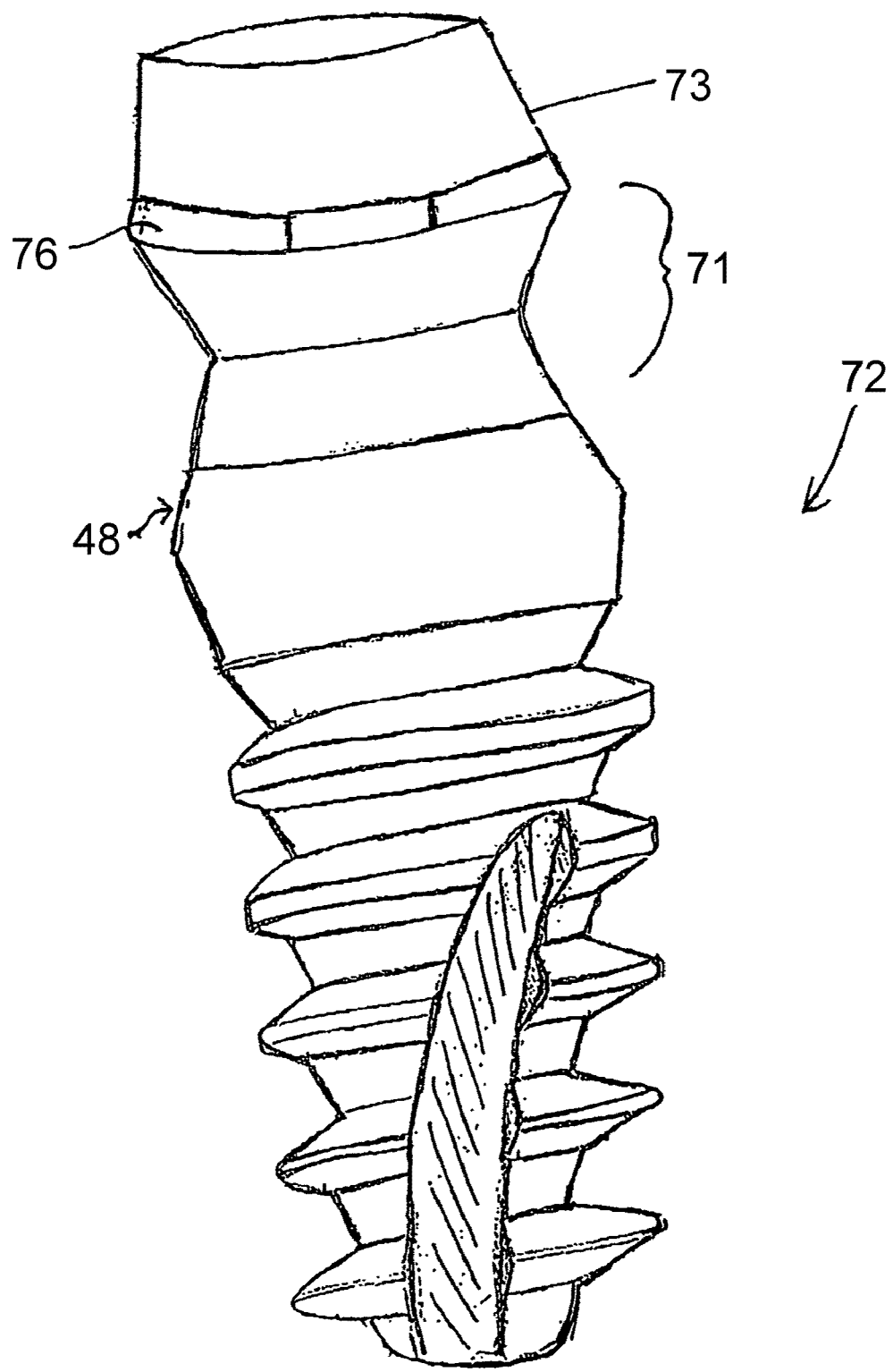
FIG. 8 is a side elevation view illustrating another embodiment of a dental implant of the present invention with an inversed tapering of the coronal end.

When an implant is completely sharply tapered as are the implants described above its most coronal region becomes very broad. This broad coronal is appropriate for regions with very low density cortical bone since it compress the cortical bone. In cases the cortical bone is not very soft this can interfere with the insertion of the implant. There are also clinical evidences that when the coronal region is broad the blood supply to the bone around the implant is disturbed resulting in higher incidence of bone resorbtion and implant failure. Therefore if the cortical bone is not very soft the coronal region preferably should be less tapered then the body of the implant. The most coronal part of the coronal region is even preferably inversed tapered 48 as illustrated in FIG. 8.

Figure 9:
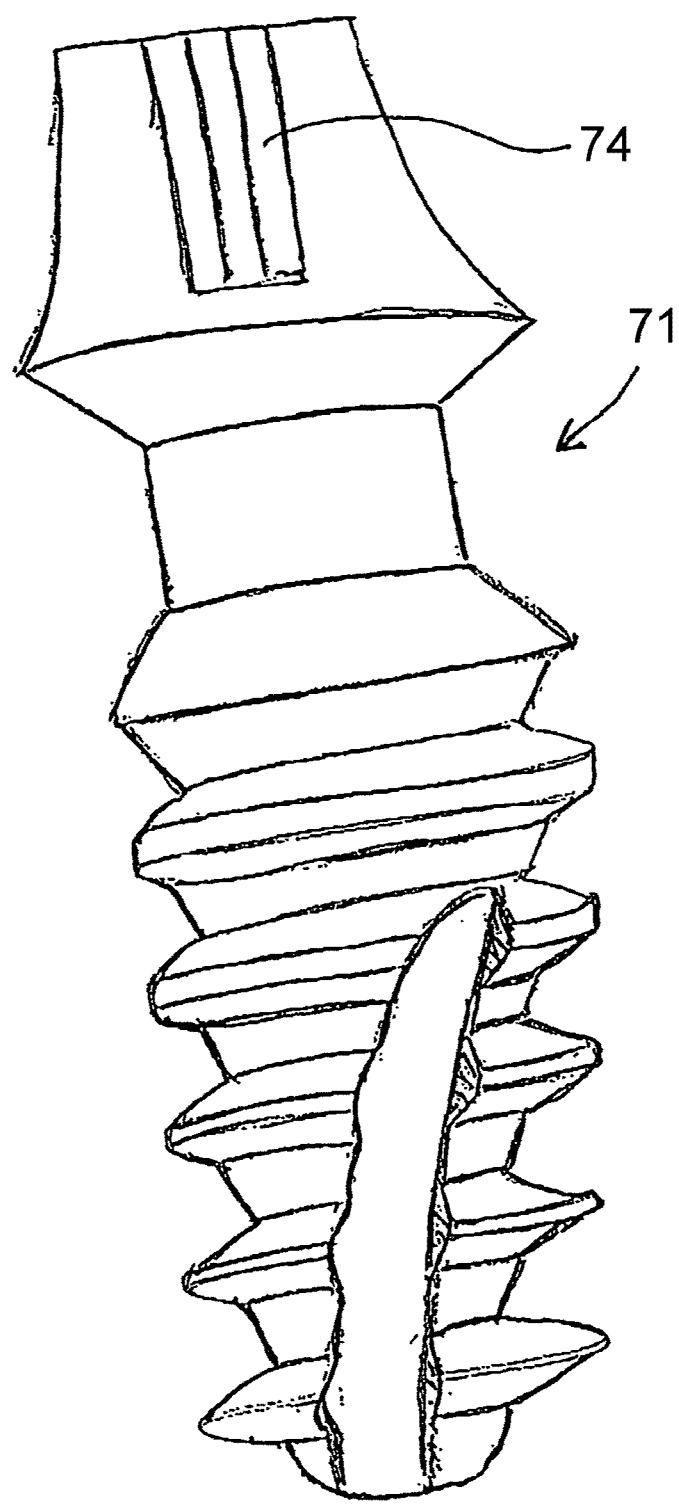
FIG. 9 is a side elevation view illustrating another embodiment of a dental implant of the present invention as one piece with the abutment.
Figure 10:
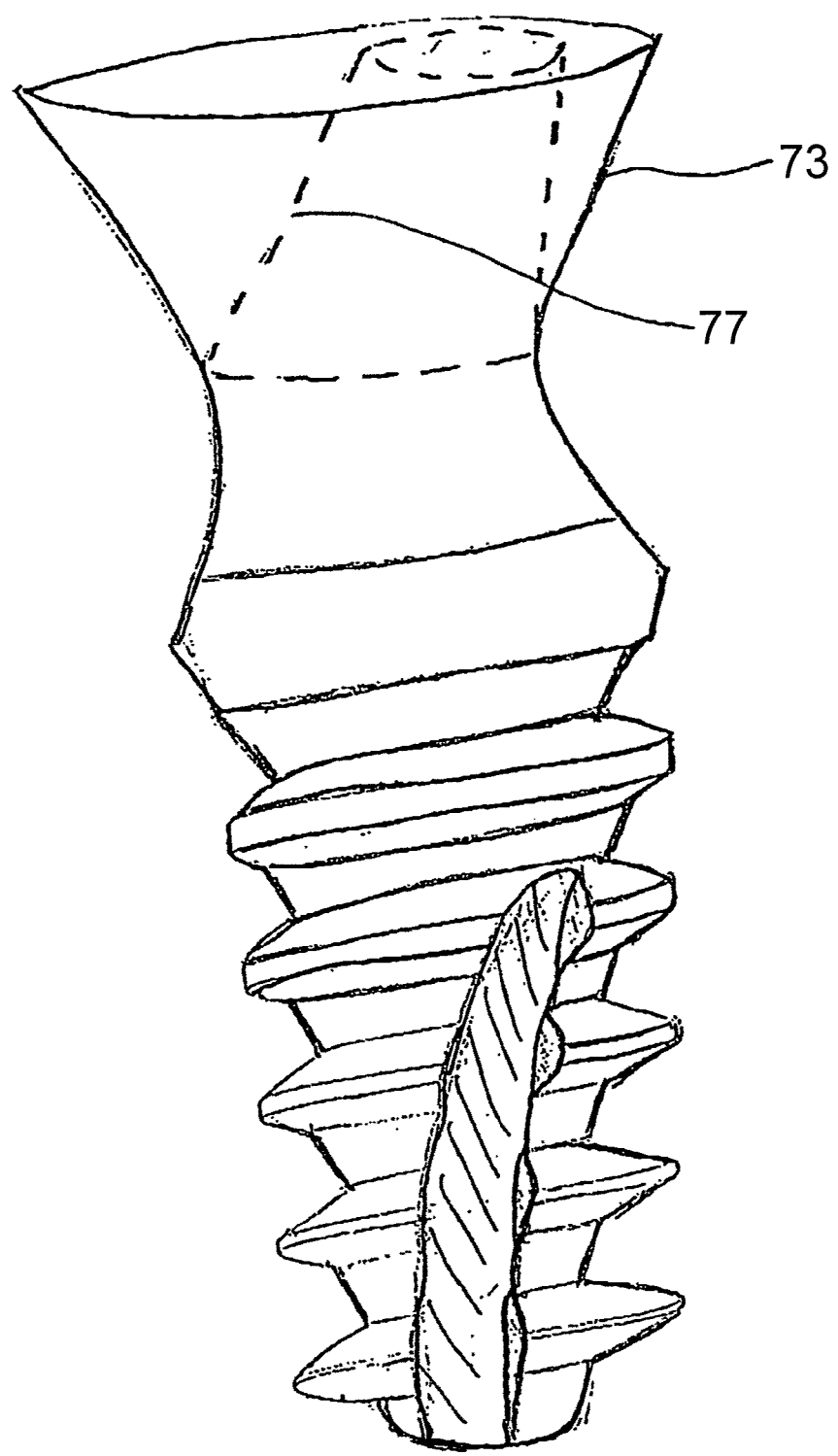
FIG. 10 is a side elevation view illustrating another embodiment of a dental implant of the present invention as one piece with the abutment.
Figure 11:
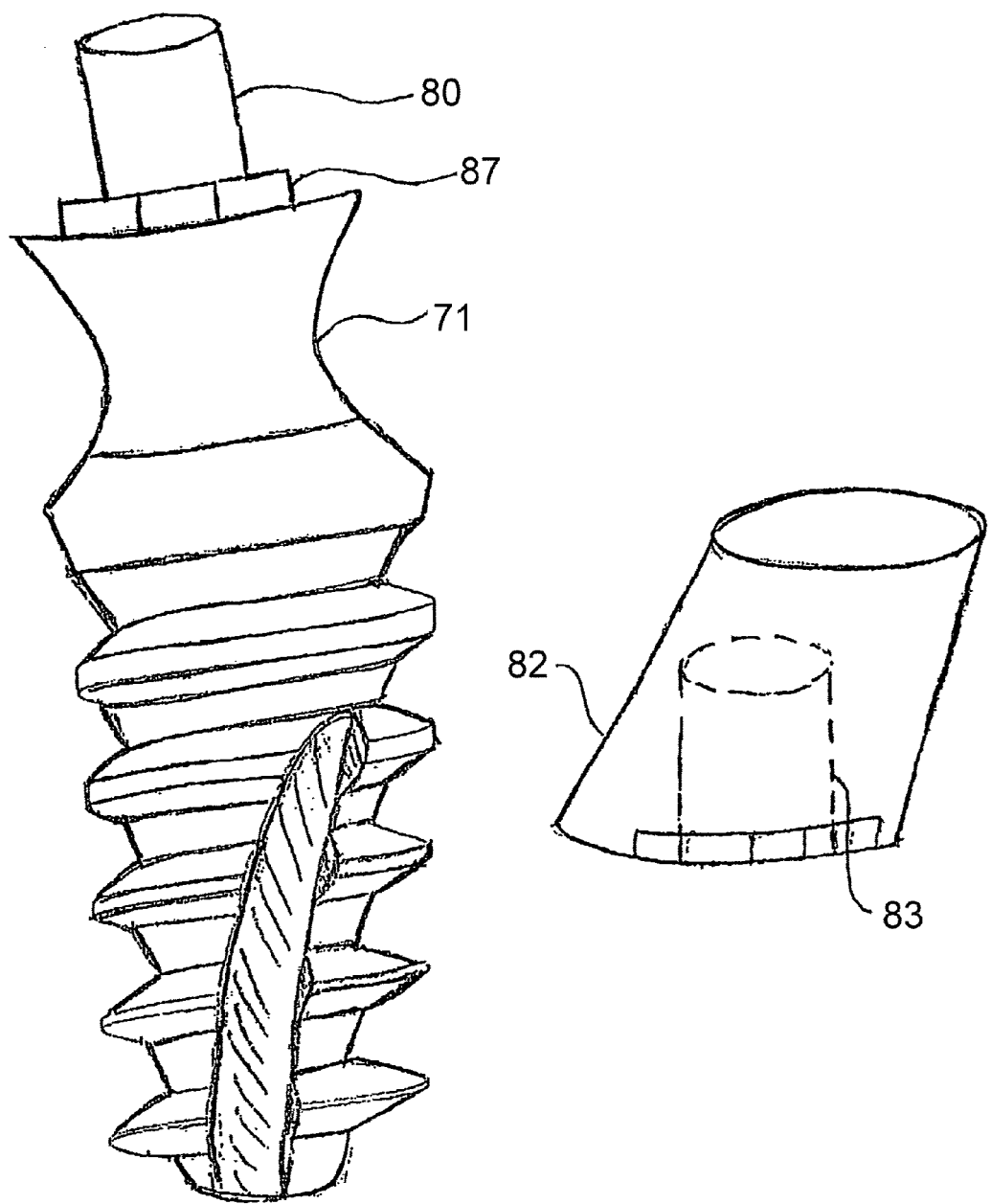
FIG. 11 is a side elevation view illustrating another embodiment of a dental implant of the present invention with an abutment for cementation.

The implant can include internal threads 63 for connection to the prosthetic part as illustrated in FIG. 5. In case the bone is very narrow the core has to be also very narrow. When the core is very narrow it can't include internal threads, so the implant can come in one piece with abutment. In these embodiments the coronal supragingival part serves for insertion of the implant and also as an abutment to support the future prosthetics. FIG. 8 illustrates such an embodiment with a narrow region 71 between the part of the implant that is to be inside the bone 72 and the abutment part 73 which is tapered to allow connection to a prosthetic element like a crown. The narrow region 71 allows good attachment of the gums to the implant therefore prevents bone loss. The abutment region can include an internal anti-rotational element or external anti-rotational element 76 that will serve for the insertion of the implant. FIG. 9 illustrates another embodiment of the novel implant as one piece with the abutment. The narrow gingival region 71 is longer than the embodiment of FIG. 8. In this embodiment an internal hexagon 74 is used for the insertion of the implant. FIG. 10 illustrates another embodiment like the embodiments of FIGS. 8 and 9 but the abutment element 73 is wider and grinding is needed to get the shape of a normal abutment like the dotted line 77. This design allows easy preparation of the abutment in cases that the implant is placed with an angle to the path of insertion of the prosthetic element. FIG. 11 resembles the implant of FIG. 10 but in this embodiment grinding the abutment of the implant is almost no needed. The implant has a round rod 80 protruding coronally above the gingival region 71. The abutment 82 has an internal bore 83 matching the round rod 80 of the implant. The abutment is tilted so after placing the abutment on the implant the angle of the abutment can be changed by rotating the abutment 82 around the rod 80. When the desired position of the abutment 82 is decided the abutment 82 can be glued to the implant. In another preferred embodiment the rod has around its base an anti rotational element 87 matching an anti-rotational element in the abutment. This configuration prevents movements of the abutment while it is cemented to the implant and can also help in taking impression of the implants to prepare the abutments in a dental laboratory.

In another preferred embodiment illustrated in FIG. 12 the coronally tapered region 85 is placed inside the bone so the bone can grow above this region. The tapered region 90 is below the bone level 91. The height of the coronally tapered region 85 is 0.5-4 mm. Preferably the height is 1-3 mm and for most cases 1.3-2.5 mm depending on the diameter of the implant.

The implant is preferably one piece because of two reasons: A. The coronal region is narrow and placing a thread or a bore inside this region will reduce the mechanical strength of the implant. B. The connection to a prosthetic element results in most cases with the creation of a micro-gap between the implant and the prosthetic element. This micro-gap can be colonized by bacteria that release toxins resulting in bone resorbtion. A one piece implant is mechanically strong and has no micro-gap.

The thread of the implant has preferably high step. The most common implants has thread step of about 0.6 mm. The present implant has preferably a thread step of 1.5-2.5 mm preferably the step is 2.1 mm. Preferably the implant has double thread meaning two threads with different beginnings running along the implant. This configuration causes that for every point of one thread there is a thread at the opposite side of the implant at the same vertical level. The threads when are inserted into the bone are creating slots. The double thread creates two opposite steep slots in the bone for every bone segment. These slots facilitate the insertion of the implant because the bone is easily expanded. The presence of two opposite slots in the bone that each one is created by a thread of more than 1.5 mm and preferably of 2.1 mm thread step allows this expansion. A regular thread of 0.6 mm will create almost horizontal slots in the bone resulting in crushing of the bone instead of expansion. Because of the slots the bone is not crushed but elastically expanded The threads begins preferably at the wider area of the coronally tapered region 92 so when this wider area reaches the bone the bone has already two points in the bone having between them approximately the diameter of this wide region so this wide region is pushing the bone at the other direction and the bone segments between the slots are displaced from each other and come back to their original location after the wide region is inserted more inside the bone. These bone segments between the slots can relapse to their original location because the coronal segment 90 is tapered coronally. This process will occur for every point along the bone where the coronally tapered region 90 is inserted inside the bone since this region is just above the beginning of the threads. The end result is a tapered region inside the bone covered with bone. Preferably threads 200 continue over the coronally tapered region 90 as illustrated in FIG. 12. In this configuration the wider region 92 is not a circle but resembles more an ellipse since the double thread that extends along the coronally tapered region reduce its diameter in one direction. This configuration facilitate the insertion of the wide region 92 inside the bone because the longer diameter of this ellipse is inserted to the slots in the bone. The insertion of a coronally tapered region with more than one thread on it allows elastic expansion of the bone and the bone is covering this tapered region after insertion inside the bone. The best results are achieved if the height of the intra-bony coronally tapered region 85 is close to the thread step. Preferably the height of the intra-bony coronaly tapered region 85 is higher than a half of the thread step.

In another preferred embodiment the threads are along the entire coronally tapered region. The threads can be the same as the threads along the implant but in another preferred embodiment can be smaller in the thread step and the thread height. The presence of a small thread or micro-thread in this region can allow better distribution of the forces to the cortical bone.

In operation, the implant can be placed into a pre-drilled osteotomy site that either matches the external diameter of the implant body, that is, the narrowest diameter between threads, or into a site that is narrower than the external diameter of the implant. Placing the implant into a narrower site will provide additional bone compression, and therefore greater initial stability. The drill can be straight or tapered. Preferably the drill is straight and the diameter is dictated by the density of the bone. For soft bone the last drill has small diameter and even insertion can be done without drilling. In hard bone a wider drill should be used and the spaces between the bone and the core of the implant will be filled with blood vessels while the implant is stabilized by the high threads.

The implant of FIG. 12 is a one piece implant that has a protruding element 93 that extends from the bone level through the gums to the oral cavity. This protruding element is preferably tapered coronally and can serve for receiving a crown like a prepared tooth. The protruding element can serve for receiving an abutment 121. This tapered protruding element 93 preferably includes an anti-rotational element of any kind. Examples of anti-rotational elements are illustrated in FIG. 13A-D. FIG. 13A illustrates several protrusions which can have an under-cut for receiving a matching transfer copping, FIG. 13B illustrates one or two protrusions or slots, FIG. 13C illustrates tapered slots, FIG. 13D illustrates a hexagon or any polygon and any other anti rotational option ellipse, stars, splines etc. The abutment 121 preferably includes a matching anti rotational element. The anti rotational element can be used with a mating transfer coping 94, an example of which is illustrated in FIG. 13D, for impressions and for the insertion of the implant. There are several types of matching abutments. FIG. 14 illustrates examples of full anatomical abutments 120. The abutments have an anatomical gingival aspect 95 which matches the subgingival and gingival anatomy of different teeth. This configuration allows the crown to emerge from the gums like a natural tooth giving the best esthetic result. The external shape 96 matches the shapes of prepared teeth. The abutment can be straight or can be angled according to the angle between the long axis of the implant and the axis of the crown. The exact location of the angled abutment is maintained by the anti-rotational element of the implant and inside the abutment. The shape can be additionally prepared to fit any particular case. The abutment has internal socket 97 matching the protruding element 93 of the implant. FIG. 14A is an example of an angled central incisor. The internal socket 97 goes through whole the abutment. In case the protruding element 93 of the implant protrudes outside the abutment as it is in FIG. 14A the excess of the protruding element can be grinded. FIG. 14B illustrates an example for an abutment for a straight premolar with an internal socket that is closed coronally. The internal socket 97 preferably is designed so most apical region of the abutment will stay above the bone level at least 0.5. For most cases 1-3 mm preferably 1.2-1.7 mm because this region has the potential to develop a micro-gap and bone resorbtion.

The abutments 121 can be bulky preferably having anatomical gingival aspect as the abutments 121 of FIG. 15. This configuration should be prepared by the dentist or at the dental laboratory to desired shape. FIG. 15A illustrates a straight bulky abutment and FIG. 15B illustrates an angled bulky abutment.

In another preferred embodiment the protruding element 93 of the implant can receive a gingival anatomical collar 122. This collar 122 matches the subgingival and gingival anatomy of different teeth and the protruding element extends through this collar coronally. The collar 122 can be of different heights or can be seated at different distances from the bone according to the width of the gingival tissue and according to esthetic consideration. Preferably the collar 122 is left above the bone level as described above for the abutments in FIGS. 14, 15. An example of a collar 122 is illustrated in FIG. 16. FIG. 16A is a side view and FIG. 16B is a top view of a collar 122 fitted on the protruding element 93 of the implant.

In case the protruding element is converging coronally by using different sockets sizes inside the abutments and collars the distance from the bone to the abutment or collar can be determined. As the socket is larger the abutment or collar can be inserted more close to the bone. The collar or abutment can be inserted at the time of inserting the implant allowing the gums to heal around the collar to receive the right shape. In this case the collar or abutments serve as a healing cap. The implant can be left without a healing cap or can receive a standard healing cap that looks like a cylindrical bulky abutment.

Figure 17G:
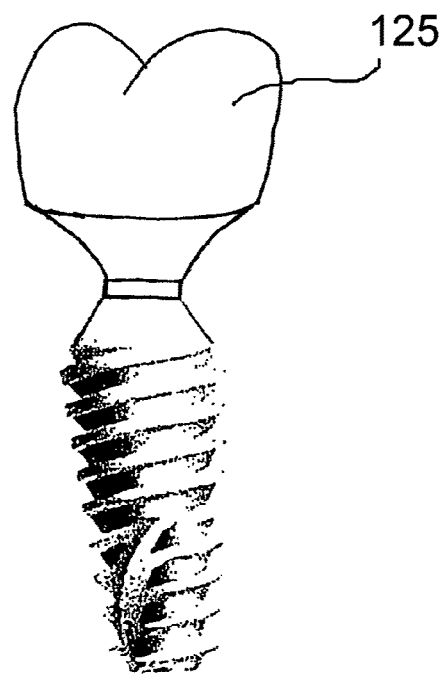
FIG. 17G is a perspective view of the implant of FIG. 17A with a crown.
Figure 17H:
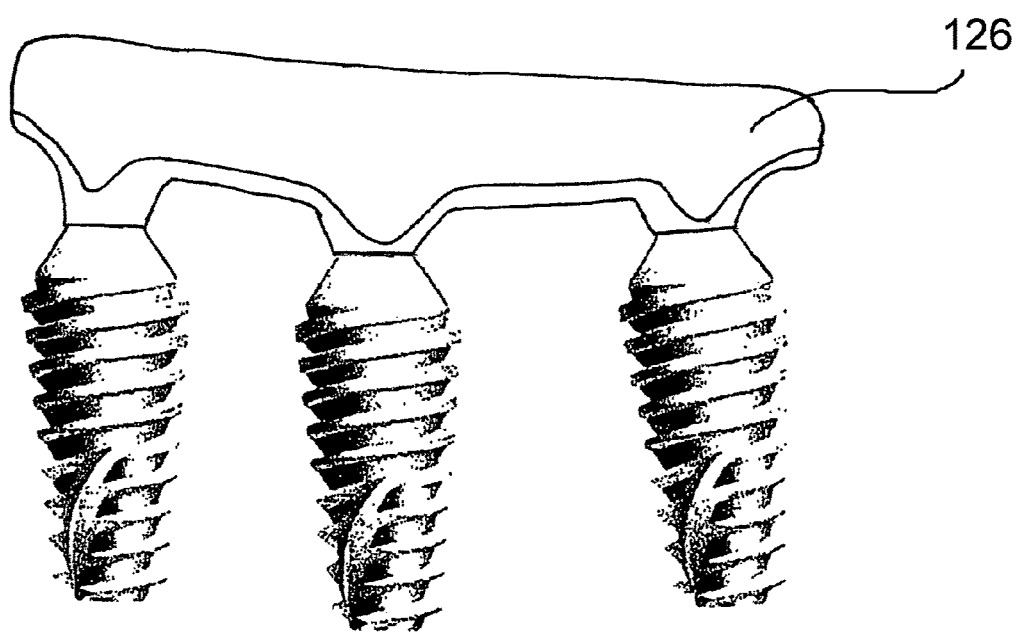
FIG. 17H is a perspective view of the implants of FIG. 17A with a bridge.

The assembly of the abutments and collars with the implant is illustrated in perspective views in FIG. 17. FIG. 17A is an example of a preferred embodiment of the implant, FIG. 17B is an example of an angled abutment 123. FIG. 17C illustrates the implant with abutment 121. FIG. 17D is a perspective view of a collar 122, FIG. 17E illustrates the implant with the collar 122. FIG. 17F illustrates the implant with a ball attachment 124. FIG. 17G illustrates the implant with a crown 125. FIG. 17H illustrates the implant with a bridge 126. The height of the protruding element 93 is reduced before the ball attachment is seated. The abutments are above the bone level 91 leaving a narrow area 98 to allow the gums to grow and seal the bone from the oral cavity. The abutments and collars can be made from any biocompatible material such as titanium zirconium or gold or from ceramic materials.

There are several ways to assure a good connection between the protruding element and the abutment or collar. The abutment or collar can be glued to the protruding element. The abutment can be manufactured to fit very accurately to the protruding element so when using some force the abutment is tightly seated over the protruding element and the friction is keeping it in place. In these cases preferably the abutment has at least one point with an under-cut to allow the dentist to take the abutment out using a crown remover. In another preferred embodiment the abutment has a locking mechanism. FIG. 18 illustrates an example of a locking mechanism. The protruding element 93 can have a small notch 99 or a slot and the abutment can have a small hole 100 placed to fit the notch 99. Into this hole 100 a small pin can be forced from the side to get inside the notch 99 and lock the abutment to the protruding element preventing it from going coronally. In another preferred embodiment, to allow taking the abutment out easily, the hole can include a thread and the abutment is locked by a small screw coming from the side into the notch or the slot 99. In another preferred embodiment illustrated in FIG. 19 the protruding element can be made of several fingers 101 and a hole 102 in the center of the protruding element. After an hollow abutment 103 is seated on the protruding element a small pin is inserted inside the hole 102 and force the fingers 101 to push the inner aspect of the abutment therefore the abutment is strongly connected to the protruding element. In another preferred embodiment at the base of the protruding element below the point where the fingers are separated there is a thread 104 and instead of a pin a small screw is screwed inside the hole to the internal thread 104. The screw has a region that its diameter is slightly larger than the diameter of the hole 102 so as the screw is inserted more deeply the fingers are pushed stronger towards the abutment. This configuration allows taking the abutment out easily.

In another preferred embodiment of a one-piece implant illustrated in FIG. 20 the abutment is seated from the side. The implant illustrated in FIG. 20A has a broad region 105 above the narrow region 98. From this broad region protrudes a low element of 0.5-3 mm height preferably of 1-2 mm with an anti-rotational mechanism like a hex 106. Above this low element 106 there is preferably a wide tapered element 107. The abutment illustrated in FIG. 20B has a slot that fits the low element 106 and the wide tapered element 107 of the implant. FIG. 20B is a perspective view of the abutment looking from the side with the slot. FIG. 20C is a side view of the abutment. The dotted line 108 shows the internal slot from the side. FIG. 20D shows the abutment of FIG. 20B-C on the implant of FIG. 20A. FIG. 20E illustrates the implant with an angled abutment. The abutments of FIG. 20 are inserted from the side to fit the anti-rotational element 106 of the implant. The abutment can't move coronally because of the wide tapered element 107 but it can move to the side. To prevent the movement to the side there are several ways 1) a matching cap 109 can be seated on top of the abutment or the crown can be used for this purpose. 2) The abutment can have holes in the walls of the slot below the height of the wide tapered element 107 so a screw or a pin can be inserted from the side below the wide tapered element 107 touching the low element 106. The hole 115 can be seen from the side in FIG. 20C. 3) A ligature can be inserted between the holes 115 and the empty space below the wide tapered element filled with a dental filling material or just the filling material like composite filling. (the abutment can have a slot all around and a ligature is placed in the slot) 4) The abutment can be manufactured to tightly fit the implant and to be inserted by force.

Figure 20C:
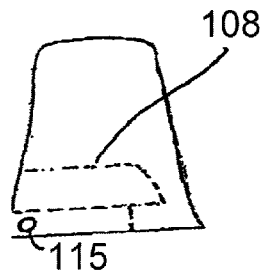
FIG. 20C is a side elevation view of the abutment of FIG. 20B.
Figure 20B:
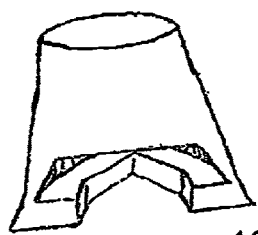
FIG. 20B is a perspective view illustrating a straight abutment to be seated from the side on the implant of FIG. 20A.
Figure 20A:
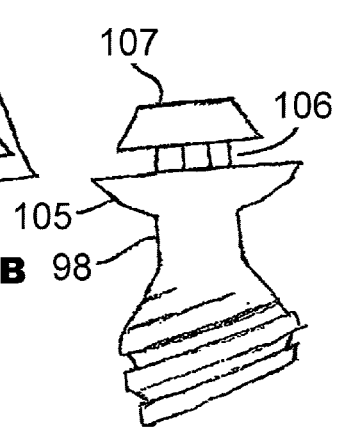
FIG. 20A is a side elevation view illustrating another embodiment of a one-piece dental implant with a coronally tapered coronal region configured to allow the abutment to be seated from the side.
Figure 20D:
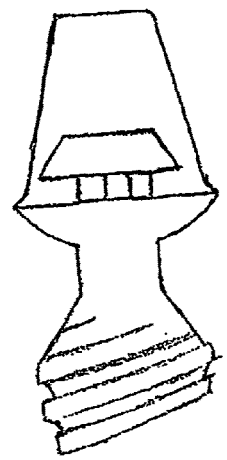
FIG. 20D is a side elevation view of the implant of FIG. 20A with the abutment of FIG. 20B.
Figure 20E:
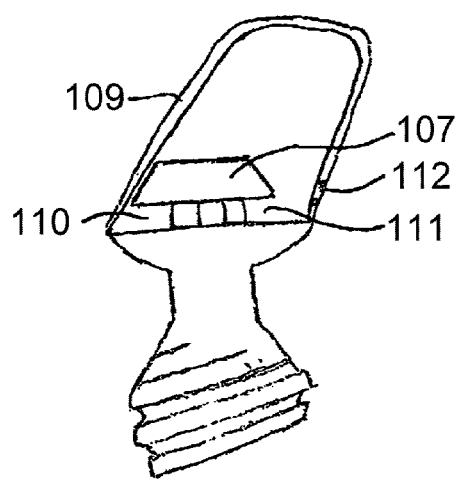
FIG. 20E is a side elevation view of the implant of FIG. 20A with an angled abutment.
Figure 20F:
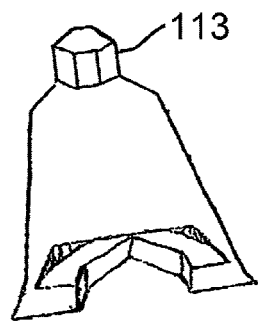
FIG. 20F is a perspective view of the abutment of FIG. 20B with an external anti-rotational element.
Figure 20G:
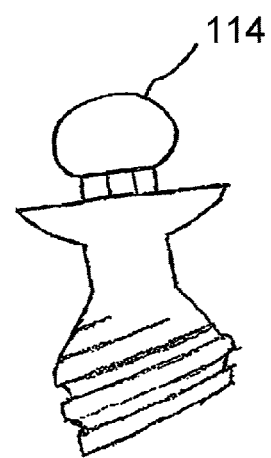
FIG. 20G is a side elevation view illustrating another embodiment of a one-piece dental implant with a spherical coronal regional configured to allow the abutment to be seated from the side or to be used as a ball attachment.
Figure 20H:
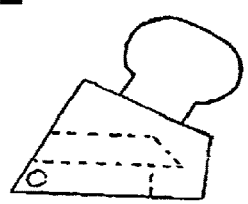
FIG. 20H is a side elevation view of an abutment with an angled ball attachment.

The slot of the angled abutment of FIG. 20E can be on the left side of the abutment of FIG. 20E meaning at the opposite side to the direction of the tilt of the angled abutment leaving an empty space 110 below the wide tapered element 107 on the left or the slot can be at the right side meaning at the direction of the tilt of the angled abutment leaving an empty space 111 below the wide tapered element 107 on the right or the slot can be in other directions in relation to the direction of the tilt of the angled abutment. The empty space when using a matching cap 109 or a crown is closed. The empty space can be filled with a dental filling material. The matching cap 109 or the crown can be cemented to abutment or the matching cap be tightly fitted to the abutment seated by friction. In a preferred embodiment the matching cap 109 or the crown are screwed to the abutment. The matching cap 109 in FIG. 20E or the crown can have a small hole preferably with a thread 112 so a small pin or a screw can be inserted through the hole to the empty space 111 (or 110 if the hole is in the other direction). This small screw is locking the abutment and the matching cap to the implant. Because there are at least two types of angled abutments, according to the location of the hole in respect to the direction of the tilt of the abutment, the dentist can decide where to place the screw for a screwed crown or bridge. The place of the screw is important for the esthetic result. If an implant is angled buccaly for all the common abutments in the market the screw is coming from buccal leaving a hole in the buccal aspect of the crown which is very difficult to cover. Screws coming from the side are known but demand a very difficult work from the laboratory. The embodiment of FIG. 20 allows having a simple screwed restoration from the side which is easily retrievable and esthetic. In another preferred embodiment the abutments of FIG. 20B and FIG. 20E have on their outer surface an anti-rotational mechanism to prevent the rotation of the matching cap or the crown. In these embodiments the matching cap and the crown have also an internal anti-rotational mechanism fitting the anti-rotational mechanism of the abutment. FIG. 20F is illustrating an embodiment of an abutment with an anti rotational mechanism like a hex 113. The wide tapered element 107 of the implant can also include an anti-rotational element preferably compatible with the anti-rotational element of the low region 106 of the implant for example both with a hex. In another preferred embodiment illustrated in FIG. 20G instead of the wide tapered region there is a spherical shape 114. This configuration allows the implant to be used as a ball attachment to support dental removable prosthesis. This preferred embodiment enables a variety of restorative possibilities: cemented restoration, screwed restorations and removable restorations. In the embodiment of FIG. 20G the healing cup instead of being inserted from the side can have an internal elastic element fitted to hold the ball 114 of the implant so the healing cap is inserted and removed vertically by some force. In another preferred embodiment the implants of FIG. 20 can also receive from the side a gingival collar as described in FIG. 16 and FIG. 17. In another preferred embodiment illustrated in FIG. 20H the abutment (or the matching cap) has an angled ball attachment. This configuration allows the dentist to achieve parallelism between the ball attachments of several implants which is difficult to achieve in the common restorative systems.

The protruding element with the anti rotational element 106-107 can be also used for the insertion of the implant and for impressions using matching transfer copings. The advantage of this embodiment is that the abutment can't be detached as long as the crown is in place and there is no need to grind the protruding element when using angled abutments or short abutments as it is the case is some of the previous embodiments The embodiment of FIG. 20 is one example but any other configuration with a protruding element that has an under-cut can function similarly to allow connection of an abutment from the side.

All the embodiment demonstrating an anti-rotational element on the implant preferably have a compatible anti-rotational element on the abutment or collar. The number of the protrusions or slots or angles of the anti-rotational element don't have to be the same for the implant and the abutment as long as the abutment can be seated on the implant.

All the abutments and collars described above can come in different heights, different widths and different angles and to be seated at different heights from the bone level. They also can have different heights and widths of the subgingival part and different heights and widths of the supragingival part.

All the embodiments of implants of the present invention can have several surfaces. The implant can have machine surface but preferably can have rough surface like TiUnite, S.L.A, Osseotite, Hydroxyapatite or bioactive surface that has growth factors and active proteins like B.M.P. The rough surface preferably is along the intrabony part of the implant and preferably also extending to the narrow region 98 of the implant.

As a result, the above embodiments provide unique advantages by providing a dental implant fixture particularly suited for use in lower density bone, such as that found in the posterior mandible and maxilla. The implant features a tapered profile and a unique external thread profile that offers superior stability when it is implanted in low density bone while insertion is easy. The implant tapers down in diameter optionally beginning at a point about 1-3 mm from below the top surface of the implant. The external thread is also tapered and changes profile from the coronal to the apical ends of the implant fixture, having a sharp, narrow and high profile at the extreme apical end, particularly suited for cutting into non-tapped bone, and having a broad, rounded and low profile at the coronal end, particularly suited for compression of bone tapped by the thread at the apical end. Further, the thread profile optionally has a flat shelf on its apical aspect, being most pronounced at the coronal end of the implant and being less pronounced at the apical end of the implant. At its coronal end, the implant has an optional flared region that acts as a mechanical stop, serving to limit over-insertion of the implant into soft bone. At its apical end, the implant optionally has a round, blunt shape and a set-back thread in the event the implant comes in advertent contact with non-osseous structures. The implant can be of one piece and have coronally converging intra-bony region near the coronal cortical bone.

The combination of all the aspect described above the coronal region, the core, the threads and the apical region allows to produce an implant that is easily inserted although the drilling is minimal, to easily dictate the location of the implant, to allow good stabilization in the bone and to allow the bone to be above the intra-bony coronally tapered region. The presence of bone above this region supports the gums and maintains their desired configuration especially the height of the gums between the teeth called papilla which is very important for the esthetic result. This bone is preserved since the implant allows drilling with a small diameter drill and the core is tapered and the threads are tapered with variable thread design and the coronal region is inversed tapered. Only the combination of all the features and the relationship between them can lead to an implant that allows the best esthetic result.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A method of installing a dental implant into a patient's jawbone, the method comprising:
    drilling an hole in the patient's jawbone for insertion of the dental implant, the hole having a diameter that is narrower than an external diameter of the dental implant;
    inserting the dental implant into the hole in the patient's jawbone, the dental implant comprising:
        a body; a coronal region of the body, the coronal region having a frustoconical shape wherein a diameter of an apical end of the coronal region is larger than a diameter of a coronal end of the coronal region; an apical region of the body, the apical region having a core with a tapered region wherein a diameter of an apical end of the core is smaller than a diameter of a coronal end of the core;
        and a helical thread extending from the body along at least a portion of the apical region,
    until a top end of the coronal region is positioned adjacent a top surface of the patient's jawbone, wherein the coronal region of the dental implant allows elastic expansion of the patient's jawbone while inserting the larger diameter apical end of the coronal region inside the patient's jawbone and after insertion of a smaller diameter coronal end of the coronal region allows the bone to relapse to cover the coronal region.

2. The method of claim 1, wherein the coronal region has a surface configured to be in contact with bone.

3. The method of claim 1, wherein the apical end of the coronal region defines an upper limit of the thread.

4. The method of claim 1, wherein the coronal region further comprises at least one groove disposed around a circumference of the coronal region.

5. The method of claim 1, wherein the thread comprises an apical side, a coronal side and a lateral edge connecting the apical side and the coronal side, the lateral edge having a variable width that expands along a segment of the apical region in the direction of the coronal end, so that a least width of the lateral edge of the thread is adjacent the apical region and a greatest width of the lateral edge of the thread is adjacent the coronal region.

6. The method of claim 5, wherein the apical end of the core is substantially flat and the lateral edge of the thread extends to an edge of the substantially flat apical end of the core such that an apical most end of the lateral edge of the thread begins at the edge of the substantially flat apical end of the core and an apical most end of the thread is self tapping.

7. The method of claim 1, wherein the thread adjacent the apical end of the core is self-tapping.

8. The method of claim 1, wherein the apical end includes a spiral tap, the spiral tap extends from one side of the implant to an opposite side along more than a third of a length of the implant.

9. The method of claim 1, wherein the implant includes a protruding element configured to protrude through a patient's gums to allow connection to a dental prosthesis.

10. The method of claim 9, wherein the protruding element and the implant are one piece.

11. The method of claim 9, wherein the protruding element is configured to be attached to an abutment from a side of the abutment.

12. The method of claim 1, wherein the hole has a diameter that matches a narrowest diameter of the apical region of the body.

13. A method of installing a dental implant, the method comprising:
    providing a dental implant having a coronal region with an inverse taper such that an apical end of the coronal region has a larger diameter than a coronal end of the coronal region, the dental implant further comprising a tapering thread body that extends from the coronal region;
    drilling a hole in the patient's jawbone for insertion of the dental implant, the hole having a diameter that is narrower than an external diameter of the dental implant; and
    inserting the dental implant into the hole in the patient's jawbone until a top end of the coronal region is positioned adjacent a top surface of the patient's jawbone, wherein the coronal region of the dental implant allows elastic expansion of the patient's jawbone while inserting the larger diameter apical end of the coronal region inside the patient's jawbone and after insertion of a smaller diameter coronal end of the coronal region allows the bone to relapse to cover the coronal region.

14. The method of claim 13 wherein thread adjacent a apical end of the body is self-tapping.

15. The method of claim 13, wherein an apical portion of the threaded tapered body includes a spiral tap.

16. The method of claim 13, wherein a thread extends to an apical end of the body, wherein the apical end of the body is substantially flat, the thread comprising:
an apical side, a coronal side, and a lateral edge connecting the apical side and the coronal side, a base connecting the thread to the body, wherein the lateral edge of the thread extends to an edge of the substantially flat apical end of the body such that an apical most end of the lateral edge of the thread begins at the edge of the substantially flat apical end of the body and an apical most end of the thread is self tapping.

17. The method of claim 13, wherein the hole has a diameter that matches a narrowest diameter of the tapering thread body.

* * * * *